United States Patent
Condeelis et al.

(10) Patent No.: US 12,298,308 B2
(45) Date of Patent: *May 13, 2025

(54) NEOADJUVANT CHEMOTHERAPY INDUCES BREAST CANCER METASTASIS THROUGH A TMEM-MEDIATED MECHANISM

(71) Applicant: Albert Einstein College of Medicine, Bronx, NY (US)

(72) Inventors: John S. Condeelis, Bronx, NY (US); Maja Oktay, Rye, NY (US)

(73) Assignee: Albert Einstein College of Medicine, Bronx, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/466,595

(22) Filed: Sep. 13, 2023

(65) Prior Publication Data
US 2024/0019439 A1 Jan. 18, 2024

Related U.S. Application Data

(63) Continuation of application No. 16/616,848, filed as application No. PCT/US2018/035013 on May 30, 2018, now Pat. No. 11,802,875.

(60) Provisional application No. 62/512,998, filed on May 31, 2017, provisional application No. 62/524,690, filed on Jun. 26, 2017.

(51) Int. Cl.
*G01N 33/574* (2006.01)
*A61K 31/337* (2006.01)
*A61K 45/06* (2006.01)

(52) U.S. Cl.
CPC ..... *G01N 33/57415* (2013.01); *A61K 31/337* (2013.01); *A61K 45/06* (2013.01); *G01N 33/5748* (2013.01)

(58) Field of Classification Search
CPC ......... G01N 33/57415; G01N 33/5748; A61K 31/337
See application file for complete search history.

(56) References Cited

U.S. PATENT DOCUMENTS

| | | | | |
|---|---|---|---|---|
| 8,603,738 | B2* | 12/2013 | Condeelis | G01N 33/5011 435/7.1 |
| 11,802,875 | B2* | 10/2023 | Condeelis | A61K 45/06 |
| 2014/0057966 | A1 | 2/2014 | Condeelis et al. | |

FOREIGN PATENT DOCUMENTS

| | | |
|---|---|---|
| WO | 2016/191401 A1 | 12/2016 |
| WO | 2017/083854 A1 | 5/2017 |

OTHER PUBLICATIONS

Karagiannis et al., "Neoadjuvant chemotherapy induces breast cancer metastasis through a TMEM-mediated mechanism", Science Translational Medicine, vol. 9, No. 397, pp. 1-17 2017).*

Daenen et al., "Chemotherapy Enhances Metastasis Formation via VEGFR-1-Expressing Endothelial Cells", Cancer Research, Nov. 2011, vol. 71, No. 22, pp. 6976-6985.

Higashi et al., "Human Mena Associated with Rac1 Small GTPase in Glioblastoma Cell Lines", Plos One, Mar. 2009, vol. 4, No. 3, p. e4765 (pp. 1-13).

Srivastava et al., "Postsurgical Adjuvant Tumor Therapy by Combining Anti-Angiopoietin-2 and Metronomic Chemotherapy Limits Metastatic Growth", Cancer Cell, Dec. 2014, vol. 26, No. 6, pp. 880-895.

* cited by examiner

*Primary Examiner* — Kevin E Weddington
(74) *Attorney, Agent, or Firm* — Fox Rothschild LLP

(57) ABSTRACT

Methods of reducing chemotherapy-induced metastasis, or chemotherapy-induced cancer cell dissemination, for patients subject to chemotherapy using Tie-2 inhibitors. Methods of reducing chemotherapy-induced metastasis, or chemotherapy-induced cancer cell dissemination, for patients subject to chemotherapy using inhibitors of Mena expression and/or function are also provided.

16 Claims, 23 Drawing Sheets

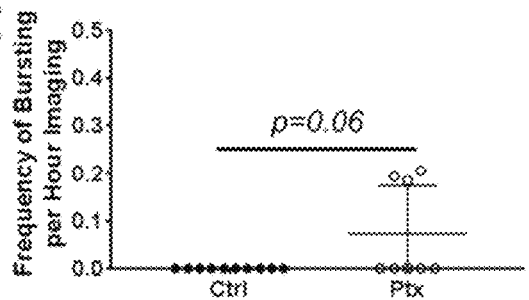
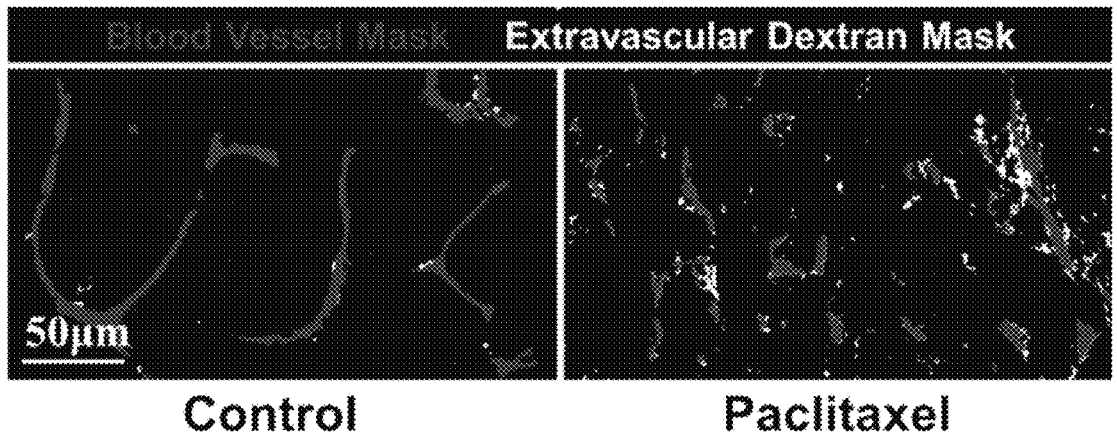
Fig. 3B-3D

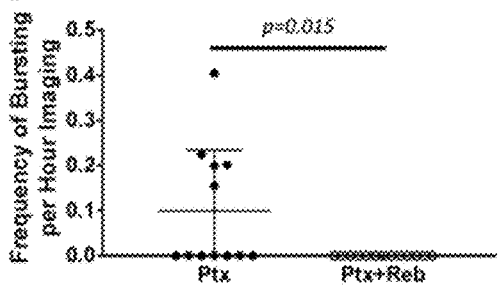
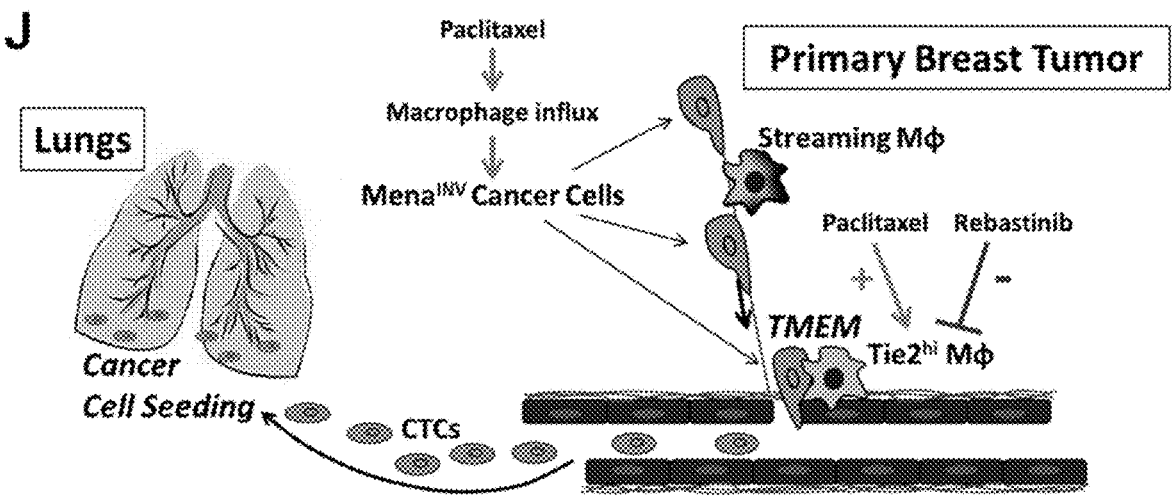
Fig. 8H-8J

NEOADJUVANT CHEMOTHERAPY INDUCES BREAST CANCER METASTASIS THROUGH A TMEM-MEDIATED MECHANISM

CROSS-REFERENCE TO RELATED APPLICATIONS

This application is a continuation of and claims priority to U.S. patent application Ser. No. 16/616,848, which is a 371 National Phase filing of International Patent Application No. PCT/US2018/35013 filed May 30, 2018, which claims benefit of U.S. Provisional Application No. 62/512,298, filed May 30, 2017, and U.S. Provisional Application No. 62/524,690, filed Jun. 26, 2017, the contents of all of which are hereby incorporated by reference.

STATEMENT OF GOVERNMENT SUPPORT

This invention was made with government support under grant numbers CA100324, CA150344, CA170507 and CA200561 awarded by the National Institutes of Health. The government has certain rights in the invention.

BACKGROUND OF THE INVENTION

Throughout this application various publications are referred to. The disclosures of these publications, and of all patents, patent application publications and books referred to herein, are hereby incorporated by reference in their entirety into the subject application to more fully describe the art to which the subject invention pertains.

Breast cancer cell intravasation and dissemination occur at microanatomical structures called Tumor MicroEnvironment of Metastasis (TMEM). Each TMEM is composed of three different cell types in direct physical contact: a tumor cell expressing the actin-regulatory protein Mammalian-enabled (Mena), a perivascular macrophage and an endothelial cell (1, 2). TMEM sites have been identified in mouse and human mammary carcinomas, and their density correlates with metastatic outcome in breast cancer patients (3-5). High-resolution intravital imaging (IVI) of murine primary breast tumors revealed that TMEM sites induce local and transient dissociation of endothelial cell junctions through which migratory cancer cells may intravasate and disseminate to secondary sites (1). TMEM-dependent vascular permeability is particularly localized, and is mediated by vascular endothelial growth factor-A (Vegf-A) release from the TMEM-bound Tie2hi/Vegfhi macrophage (1).

Randomized prospective studies indicate that addition of paclitaxel into the preoperative neoadjuvant chemotherapy (NAC) regimen significantly increases the rate of pathologic complete response (pCR), but paradoxically does not improve the overall survival (6, 7). It has been also shown in mouse breast cancer models that taxane-based chemotherapies, if discontinued, promote tumor regrowth by inducing angiogenesis. In particular, they mobilize bone marrow-derived mesenchymal and endothelial progenitors and CD11b+ myeloid cells, including Tie2+ monocytes, into the primary tumor microenvironment (8-13). Tie2+ monocyte progenitors transform into Tie2hi macrophages, which associate with newly constructed tumor blood vessels and promote tumor regrowth (14, 15). As stated before, Tie2hi macrophages are also critical constituents of the functional TMEM sites, where they mediate Vegf-induced blood vessel permeability and tumor cell intravasation.

TMEM-dependent vascular permeability is necessary but not sufficient for tumor cell intravasation, because intravasation also requires presence of discohesive, migratory cancer cells (1, 16-18). These migratory cells express high levels of invasive, chemotactic pro-metastatic Mena isoform $Mena^{INV}$, and low levels of the anti-metastatic Mena isoform, Mena11a (18-26). We have previously documented that $Mena^{INV}$ expression is switched on in invasive tumor cells by Notch-mediated macrophage contact and signaling (27). Furthermore, it is known that paclitaxel induces influx of macrophages into the primary tumor which are required for TMEM assembly and function (1, 2, 19, 20, 28, 29)

The present invention addresses the need for improved anti-metastatic therapies, including for patients with localized disease treated with chemotherapy before the removal of the primary tumor (neoadjuvant setting).

SUMMARY OF THE INVENTION

A method of treating a subject for a tumor, wherein the subject has received or is receiving chemotherapy treatment for the tumor, comprising
  a) identifying the subject as having an increased risk of metastasis in response to chemotherapy by performing or having performed a quantification of $Mena^{Calc}$, $Mena^{INV}$ or a TMEM score of the tumor, and comparing to a predetermined control level of $Mena^{Calc}$, $Mena^{INV}$ or TMEM score, wherein a subject having a $Mena^{Calc}$, $Mena^{INV}$ or a TMEM score above the respective predetermined control level identifies the subject as having an increased risk of metastasis, and
  b) when a subject is identified in step a) as having an increased risk of metastasis in response to chemotherapy, either (1) ceasing chemotherapy on the subject and administering a targeted therapy, immunotherapy or radiotherapy to treat the cancer, or (2) administering a chemotherapy and an amount of (i) a Tie-2 inhibitor effective to reduce chemotherapy-induced metastasis or chemotherapy-induced cancer cell dissemination, or
  (ii) a TMEM activity inhibitor, to the subject effective to treat a tumor.

A method of reducing chemotherapy-induced metastasis, or chemotherapy-induced cancer cell dissemination, comprising administering, to a patient with a cancer subject to a chemotherapy treatment, an amount of (i) an inhibitor of Mena function or (ii) an inhibitor of Mena expression effective to reduce chemotherapy-induced metastasis or chemotherapy-induced cancer cell dissemination.

A method of reducing chemotherapy-induced tumor microenvironment of metastasis (TMEM) activity in a patient comprising administering, to a patient with a cancer subject to a chemotherapy treatment, an amount of (i) an inhibitor of Mena function or (ii) an inhibitor of Mena expression effective to reduce chemotherapy-induced TMEM activity.

A method of inhibiting metastasis of a cancer comprising administering, to a patient with a cancer, an amount of (i) an inhibitor of Mena function or (ii) an inhibitor of Mena expression effective to inhibit metastasis of a cancer.

A method of reducing chemotherapy-induced metastasis, or chemotherapy-induced cancer cell dissemination, is provided comprising administering, to a patient with a cancer subject to a chemotherapy treatment, an amount of a Tie-2 inhibitor effective to reduce chemotherapy-induced metastasis or chemotherapy-induced cancer cell dissemination.

Also provided is a method of reducing chemotherapy-induced tumor microenvironment of metastasis (TMEM)

activity in a patient comprising administering, to a patient with a cancer subject to a chemotherapy treatment, an amount of a Tie-2 inhibitor effective to reduce chemotherapy-induced TMEM activity.

Also provided is a method of inhibiting metastasis of a cancer comprising administering, to a patient with a cancer, an amount of a Tie-2 inhibitor effective to inhibit metastasis of a cancer.

A method for identifying a subject as likely having a poor long-term response to chemotherapy comprising determining, in a sample obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a poor long-term response to chemotherapy wherein a subject is identified as likely having a poor long-term response to chemotherapy when the sample obtained from the subject has a level of Mena$^{Calc}$, Mena$^{INV}$ or TMEM score above the predetermined control level of Mena$^{Calc}$, Mena$^{INV}$ or TMEM score, respectively.

A method for identifying a subject as likely having a tumor resistant to a receptor tyrosine kinase (RTK) inhibitor therapy comprising determining, in a sample of the tumor obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a tumor resistant to RTK inhibitor therapy, wherein a subject is identified as likely having a tumor resistant to RTK inhibitor therapy when the sample obtained from the subject has a level of Mena$^{Calc}$, Mena$^{INV}$ or TMEM score above the predetermined control level of Mena$^{Calc}$, Mena$^{INV}$ or TMEM score, respectively.

A method for identifying a subject as likely having a tumor resistant to a receptor tyrosine kinase (RTK) inhibitor and cytotoxic chemotherapy combination therapy comprising determining, in a sample of the tumor obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a tumor resistant to RTK inhibitor and cytotoxic chemotherapy combination therapy, wherein a subject is identified as likely having a tumor resistant to RTK inhibitor therapy and cytotoxic chemotherapy combination therapy when the sample obtained from the subject has a level of Mena$^{Calc}$, Mena$^{INV}$ or TMEM score above the predetermined control level of Mena$^{Calc}$, Mena$^{INV}$ or TMEM score, respectively.

BRIEF DESCRIPTION OF THE DRAWINGS

FIG. 3A-3J. Paclitaxel Promotes TMEM-Dependent Vascular Permeability, Cancer Cell Dissemination and Metastasis in Breast Cancer. (A) Time lapse images of Supplementary Videos 1 (upper row) and 2 (lower row). Time shown in minutes (t=0'-20'). Arrowhead; site of bursting in a paclitaxel-treated mouse (active TMEM). (B) Incidence of bursting (at least 1 complete event during 4.5-h of imaging per mouse) in paclitaxel-treated and vehicle-treated MMTV-PyMT/Dendra2 cfms-CFP mice. (C) Frequency of bursting in paclitaxel and control MMTV-PyMT/Dendra2 cfms-CFP mice. Mann-Whitney U-test. (D) Representative blood vessel (endomucin) and extravascular dextran masks, as obtained by IF in mice treated with either vehicle or paclitaxel, showing TMEM-associated vascular permeability. (E) Quantification of extravascular dextran area normalized to blood vessel area in mice treated with either vehicle or paclitaxel shown in D. Mann-Whitney U-test. (F) Circulating tumor cells per mL of blood collected before sacrifice (day 15). Values normalized to the control group in each case to account for inter-cohort variability. Mann-Whitney U-test. (G) Correlation between CTCs and TMEM ($R^2$=Pearson's Coefficient of Determination); filled circles, control; open circles, paclitaxel. (H) Incidence of lung metastasis in mice treated with paclitaxel or vehicle control. Lower panels show two cases of histologically-detectable metastases in lungs of PyMT-transplants and HT17-xenografts, respectively. (I) Quantification of histologically-detectable lung metastases in mice treated with paclitaxel or vehicle control. Mann-Whitney U-test. (J) Left: Quantification of single cancer cell dissemination in lungs of PyMT-transplants using fluorescent stereomicroscopy. Right: Blood vessels visualized via tail-vein injection of rhodamine-labeled lectin 1-h before sacrifice and cancer cells identified through Dendra2 expression (arrow). Mann-Whitney U-test.

Figures 1A, 1B:
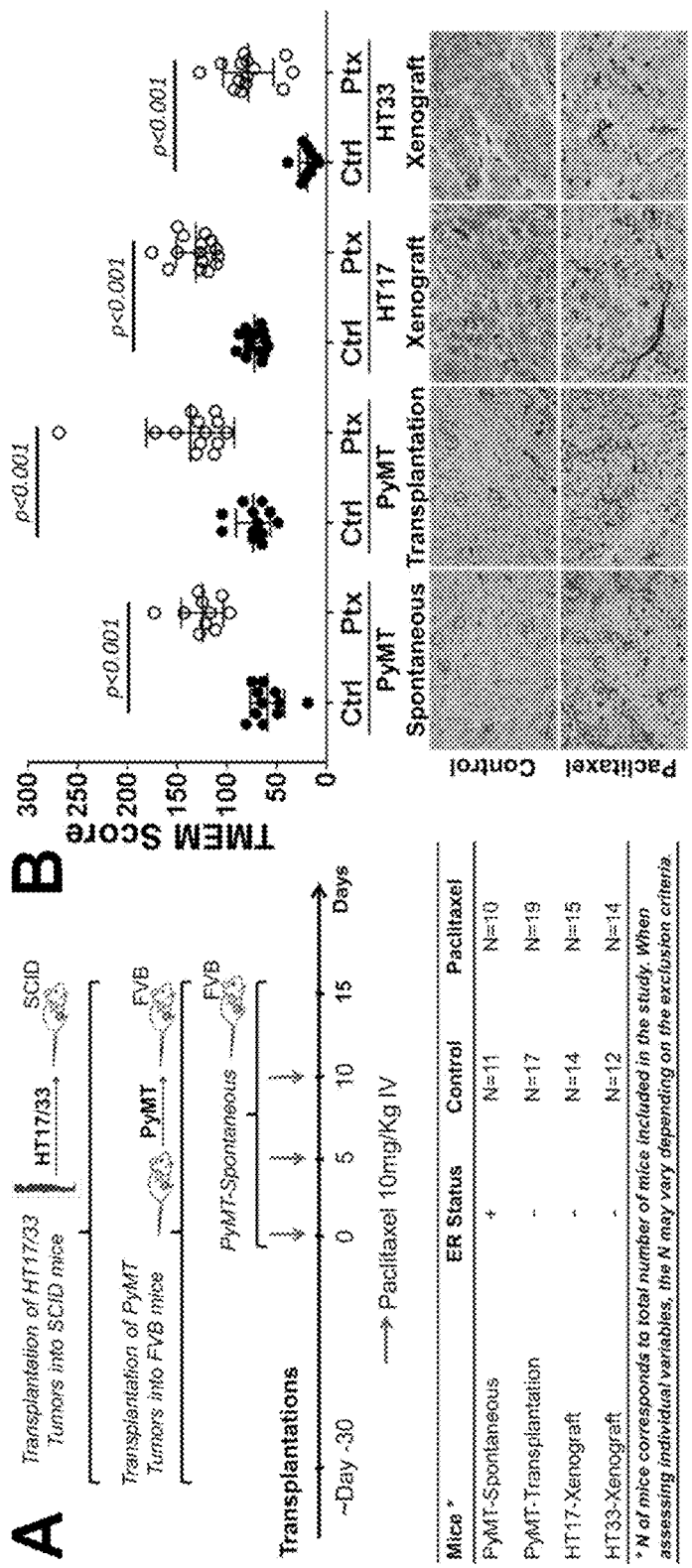
FIG. 1A-1H. Paclitaxel Delays Tumor Growth while Promoting Infiltration of Tie2$^{hi}$/Vegf$^{hi}$ Macrophages and TMEM Assembly: (A) Experimental design and cohort composition. (B) TMEM score in mice treated as shown in the experimental design and TMEM identification by triple-stain immunohistochemistry (IHC). Upper graph, TMEM score assessed in 10 high-power fields (HPFs) by two pathologists; lower panel, representative images for each mouse model. Mann-Whitney U-test. (C) Perivascular Iba1$^+$ macrophages in 10 HPFs (absolute counts) in PyMT-spontaneous and HT17-xenograft tumors treated with paclitaxel or vehicle control. Mann-Whitney U-test. (D) Perivascular Tie2$^{hi}$/Vegf$^{hi}$ macrophages in 10 HPFs (absolute counts) quantified in PyMT-spontaneous and HT17-xenograft tumors, treated with paclitaxel or vehicle control. Mann-Whitney U-test. (E) Immunofluorescence (IF) of Iba1, Cd31, Tie2, Vegf and DAPI in two sequential sections of an MMTV-PyMT breast tumor not treated with paclitaxel. Representative Vegf$^{hi}$/Tie2$^{hi}$ macrophage (also co-expressing Iba1) encircled with yellow dotted line (F) IF of Iba1, Cd31, Vegf and DAPI in an HT17-xenograft tumor treated with paclitaxel, demonstrating a Vegf$^{hi}$ and a Vegf$^{lo}$ macrophage in the same field of view. (G-H) Correlations of macrophage infiltration (Iba1$^+$ macrophages or Vegf$^{hi}$/Tie2$^{hi}$ macrophages) with TMEM Score in the PyMT-spontaneous (G) and HT17-xenograft (H) models ($R^2$=Pearson's Coefficient of Determination); filled circles, control; open circles, paclitaxel.

Therefore, agents that block Mena expression and/or that inhibit the interaction of Mena with its target proteins, including PTP1b, SHIP2, Rac1 and the RTKs mentioned in the claims (see Eddy et al 2017 TICB FIGS. 1 and 2), will inhibit the same activities claimed for the TIE2 inhibitors.

FIG. 6A-6E: Pro-metastatic changes of the breast tumor microenviroment may be also mediated by chemotherapies other than taxanes. (A) Experimental design and cohort composition. (B) Representative histological (H & E) and TMEM IHC sections in 40× magnification from PyMT mice receiving doxorubicin/cyclophosphamide treatment or vehicle control, as shown in A. (C) TMEM score in MMTV-PyMT mice treated with either vehicle-control or doxorubicin/cyclophosphamide. Mann-Whitney U-test. (D) Circulating tumor cells per mL of blood collected before sacrifice (day 15). Values normalized to the control group in each case, to account for inter-cohort variability. Mann-Whitney U-test. (E) Proportion of perivascular Tie2$^{hi}$/Vegf$^{hi}$ macrophages among all Iba1$^+$ macrophages, quantified in MMTV-PyMT mice treated with either or doxorubicin/cyclophosphamide or vehicle control. Mann-Whitney U-test.

FIG. 7A-7F: Neoadjuvant Chemotherapy in Breast Cancer Patients Promotes TMEM Assembly and Increased Mena$^{INV}$ Expression. (A) Individual TMEM scores of 20 patients before and after receiving NAC, which included weekly paclitaxel (80 mg/m$^2$×12 consecutive weeks) followed sequentially by dose-dense AC chemotherapy (doxorubicin 60 mg/m2 and cyclophosphamide 600 mg/m2 every 2 weeks×4 cycles, plus pegrastim 6 mg SC on day 2 of each cycle). The patients did not receive Tamoxifen. Red line; TMEM high-risk cutoff point (5). (B) Representative images of TMEM triple-stain IHC in patients #3 and #7 in the pre-NAC core biopsies (upper panels) and post-NAC resected tumors (lower panels). (C) Mean TMEM scores in the 20 human breast cancers shown in A, before and after receiving NAC. Wilcoxon test. (D) Representative images of Mena$^{INV}$ protein expression, as visualized by Mena$^{INV}$ immunofluorescence and DAPI in a patient receiving NAC. (E) Quantification of the Mena$^{INV}$-positive area in pre- and post-NAC patient samples. Assay performed in only 7 of the patients shown in A, because of limited availability of pre-NAC biopsy material for the remaining 13 patients. Mann-Whitney U-test. (F) Mena$^{INV}$ gene expression, as assessed by real-time RT-PCR, in fine needle aspiration (FNA) biopsies taken from 5 breast cancer patients before and after 2-weeks of receiving NAC with paclitaxel.

FIG. 8A-8J: The Tie2 Inhibitor Rebastinib Eliminates the Pro-metastatic Effects of Paclitaxel. (A) Experimental design and cohort composition. (B-C) TMEM scores in the PyMT-transplantation model (B) and the HT17-xenograft model (C), treated with vehicle control or rebastinib, or paclitaxel, or combination of rebastinib with paclitaxel. Mann-Whitney U-test. (D-E) Perivascular Tie2$^{hi}$/Vegf$^{hi}$ macrophages quantified in 10 HPFs in the PyMT-transplantation model (D) or in the HT17-xenograft model (E), treated with vehicle control or rebastinib or paclitaxel or combination of rebastinib with paclitaxel. Mann-Whitney U-test. (F-G) Circulating tumor cells/mL of blood collected before sacrifice (day 15) of mice (PyMT-transplantation, F; HT17-xenograft, G). Values normalized to the control group in each case to account for inter-cohort variability. Mann-Whitney U-test. (H) Incidence of bursting (at least 1 complete event during 4.5-h of imaging per mouse) in paclitaxel-treated MMTV-PyMT/Dendra2 cfms-CFP mice that either received or did not receive rebastinib. (I) Frequency of bursting in paclitaxel-treated MMTV-PyMT/Dendra2 cfms-CFP mice that either received or did not receive rebastinib. Mann-Whitney U-test. (J) Proposed Model of chemotherapy-induced pro-metastatic changes and Cancer Cell Dissemination. Chemo treatment increases the density of Tie2$^{hi}$/Vegf$^{hi}$ macrophages within the primary tumor. Besides inducing angiogenesis, these macrophages assemble active TMEM structures. Paclitaxel treatment also increases expression of the actin-regulatory protein Mena$^{INV}$ isoform in tumor cells due to their contact with infiltrating macrophages, which in turn generates a highly-migratory and invasive subpopulation of cancer cells and TMEM assembly. Together, paclitaxel-mediated TMEM-assembly and Mena$^{INV}$ overexpression in breast cancer contribute to TMEM-dependent cancer cell dissemination and distant metastasis. Targeting the function of TMEM-associated macrophage subpopulation by Tie2 inhibitors counter-acts TMEM-mediated cancer cell dissemination induced by paclitaxel treatment.

DETAILED DESCRIPTION OF THE INVENTION

A method of treating a subject for a tumor, wherein the subject has received or is receiving chemotherapy treatment for the tumor, comprising
  a) identifying the subject as having an increased risk of metastasis in response to chemotherapy by performing or having performed a quantification of $Mena^{Calc}$, $Mena^{INV}$ or a TMEM score of the tumor, and comparing to a predetermined control level of $Mena^{Calc}$, $Mena^{INV}$ or TMEM score, wherein a subject having a $Mena^{Calc}$, $Mena^{INV}$ or a TMEM score above the respective predetermined control level identifies the subject as having an increased risk of metastasis, and
  b) when a subject is identified in step a) as having an increased risk of metastasis in response to chemotherapy, either (1) ceasing chemotherapy on the subject and administering a targeted therapy, immunotherapy or radiotherapy to treat the cancer, or (2) administering a chemotherapy and an amount of (i) a Tie-2 inhibitor effective to reduce chemotherapy-induced metastasis or chemotherapy-induced cancer cell dissemination, or (ii) a TMEM activity inhibitor, to the subject effective to treat a tumor.

In an embodiment, wherein when a subject is identified in step a) as having an increased risk of metastasis in response to chemotherapy, the chemotherapy and an amount of (i) a Tie-2 inhibitor effective to reduce chemotherapy-induced metastasis or chemotherapy-induced cancer cell dissemination, or (ii) a TMEM activity inhibitor, is administered to the subject.

In embodiments, wherein the TMEM activity inhibitor comprises a CSF1R inhibitor, a VEGFR inhibitor, or a MENA inhibitor.

In embodiments, the method further comprises obtaining a predetermined control level for $Mena^{Calc}$, $Mena^{INV}$ or TMEM score for the subject by obtaining a $Mena^{Calc}$, $Mena^{INV}$ or TMEM score from a tumor sample from the subject prior to any chemotherapy being initiated on the subject.

In embodiments, the Tie-2 inhibitor is administered.

In embodiments, the Tie-2 inhibitor is rebastinib (4-[4-[(5-tert-butyl-2-quinolin-6-ylpyrazol-3-yl)carbamoylamino]-3-fluorophenoxy]-N-methylpyridine-2-carboxamide).

In embodiments, the chemotherapy is an anti-tubulin chemotherapy.

In embodiments, the chemotherapy is a taxane.

In embodiments, the chemotherapy is paclitaxel or eribulin.

In embodiments, the tumor is a breast cancer tumor.

In embodiments, the breast cancer is an adenocarcinoma.

In embodiments, the breast cancer is Human Epidermal Growth Factor 2 Negative.

In embodiments, the breast cancer is a recurrent breast carcinoma.

In embodiments, the breast cancer is a Stage IV breast cancer.

In embodiments, the chemotherapy is a neoadjuvant therapy.

In embodiments, the metastasis is a lung metastasis, bone metastasis, lymph node metastasis, liver metastasis or brain metastasis.

In embodiments, the method may be performed when the patient has started chemotherapy within the last day or week. In embodiments, the method may be performed when the patient has been on a course of chemotherapy. In embodiments the method may be performed so as to determine the future treatment of the tumor in the subject. In embodiments the method may be performed so as to determine the effectiveness of the current treatment of the tumor in the subject and/or make treatment decisions.

A method of reducing chemotherapy-induced metastasis, or chemotherapy-induced cancer cell dissemination, comprising administering, to a patient with a cancer subject to a chemotherapy treatment, an amount of (i) an inhibitor of Mena function or (ii) an inhibitor of Mena expression effective to reduce chemotherapy-induced metastasis or chemotherapy-induced cancer cell dissemination.

A method of reducing chemotherapy-induced tumor microenvironment of metastasis (TMEM) activity in a patient comprising administering, to a patient with a cancer subject to a chemotherapy treatment, an amount of (i) an inhibitor of Mena function or (ii) an inhibitor of Mena expression effective to reduce chemotherapy-induced TMEM activity.

A method of inhibiting metastasis of a cancer comprising administering, to a patient with a cancer, an amount of (i) an inhibitor of Mena function or (ii) an inhibitor of Mena expression effective to inhibit metastasis of a cancer.

In an embodiment, the inhibitor of Mena is an interfering-RNA, an interfering-microRNA, a Mena gene edit, or a Mena gene splicing suppressor. In an embodiment, the inhibitor of Mena is an inhibitor of Mena function and is a small molecule inhibitor of, or an aptamer which inhibits, Mena's interaction with a target protein. In an embodiment, the inhibitor of Mena is an inhibitor of Mena's interaction with a target protein which is PTP1b, SHIP2, Rac1 or a receptor tyrosine kinase.

In an embodiment, two or more Mena splice variants are suppressed by the inhibitor of Mena. In an embodiment, all Mena splice variants are suppressed by the inhibitor of Mena. This is effective since Mena is tetrameric and can be partially functional even when only a subset of isoforms are expressed (Eddy et al 2017).

A method of reducing chemotherapy-induced metastasis, or chemotherapy-induced cancer cell dissemination, is provided comprising administering, to a patient with a cancer subject to a chemotherapy treatment, an amount of a Tie-2 inhibitor effective to reduce chemotherapy-induced metastasis or chemotherapy-induced cancer cell dissemination.

In an embodiment, the Tie-2 inhibitor is rebastinib (4-[4-[(5-tert-butyl-2-quinolin-6-ylpyrazol-3-yl)carbamoylamino]-3-fluorophenoxy]-N-methylpyridine-2-carboxamide).

In an embodiment of the methods, the patient has a localized cancer treated with neoadjuvant chemotherapy. In an embodiment, the patient has metastatic disease treated with chemotherapy.

In an embodiment of the methods, the chemotherapy is an anti-tubulin chemotherapy.

In an embodiment of the methods, the chemotherapy comprises administering a taxane.

In an embodiment of the methods, the chemotherapy comprises administering paclitaxel or eribulin.

In an embodiment of the methods, the cancer is a breast cancer.

In an embodiment of the methods, the breast cancer is an adenocarcinoma.

In an embodiment of the methods, the breast cancer is Human Epidermal Growth Factor 2 Negative. In an embodiment, the breast cancer is estrogen and/or progesterone hormone receptor positive. In an embodiment, the breast cancer is Her2/Neu positive. In an embodiment, the breast cancer is triple negative. In an embodiment, the breast cancer is estrogen and/or progesterone positive/Her2Neu positive.

In an embodiment of the methods, the breast cancer is a recurrent breast carcinoma.

In an embodiment of the methods, the breast cancer is localized breast cancer (stages I-III). In an embodiment, the breast cancer is metastatic disease (stage IV). In an embodiment, the breast cancer is carcinoma in situ (stage 0).

In an embodiment of the methods, the chemotherapy is a neoadjuvant therapy.

In an embodiment of the methods, the metastasis is a lung metastasis, bone metastasis, lymph node metastasis, liver metastasis or brain metastasis. In an embodiment, the metastasis is any recurrence of the disease in a distant site including, but not limited to, lung, bone, lymph node, liver or brain.

In an embodiment of the methods, the method is for reducing chemotherapy-induced metastasis.

In an embodiment of the methods, the method is for reducing chemotherapy-induced cancer cell dissemination.

Also provided is a method of reducing chemotherapy-induced tumor microenvironment of metastasis (TMEM) activity in a patient comprising administering, to a patient with a cancer subject to a chemotherapy treatment, an amount of a Tie-2 inhibitor effective to reduce chemotherapy-induced TMEM activity.

In an embodiment, the Tie-2 inhibitor is rebastinib (4-[4-[(5-tert-butyl-2-quinolin-6-ylpyrazol-3-yl)carbamoylamino]-3-fluorophenoxy]-N-methylpyridine-2-carboxamide).

In an embodiment of the methods, the patient has a localized cancer treated with neoadjuvant chemotherapy. In an embodiment, the patient has metastatic disease treated with chemotherapy.

In an embodiment of the methods, the chemotherapy is a neoadjuvant therapy.

In an embodiment of the methods, the chemotherapy is a taxane (e.g. paclitaxel), a non-taxane microtubule inhibitors (e.g. eribulin), a topoisomerase inhibitor (e.g. etoposide), an intercalating agent (e.g. doxorubicin), a DNA cross-linking agent (e.g. cisplatin), an alkylating agent (e.g. cyclophosphamide). In an embodiment, the chemotherapy is a combination of two or more of said chemotherapies.

In an embodiment of the methods, the chemotherapy is an anti-tubulin chemotherapy.

In an embodiment of the methods, the chemotherapy comprises administering a taxane.

In an embodiment of the methods, the chemotherapy comprises administering paclitaxel or eribulin.

In an embodiment of the methods, the neoadjuvant therapy comprises doxorubicin and cyclophosphamide.

In an embodiment of the methods, the cancer is a breast cancer.

In an embodiment of the methods, the breast cancer is an adenocarcinoma.

In an embodiment of the methods, the breast cancer is Human Epidermal Growth Factor 2 Negative. In an embodiment, the breast cancer is estrogen and/or progesterone hormone receptor positive. In an embodiment, the breast cancer is Her2/Neu positive. In an embodiment, the breast cancer is triple negative. In an embodiment, the breast cancer is estrogen and/or progesterone positive/Her2Neu positive.

In an embodiment, the breast cancer is a recurrent breast carcinoma.

In an embodiment, the breast cancer is localized breast cancer (stages I-III). In an embodiment, the breast cancer is metastatic disease (stage IV). In an embodiment, the breast cancer is carcinoma in situ (stage 0).

Also provided is a method of inhibiting metastasis of a cancer comprising administering, to a patient with a cancer, an amount of a Tie-2 inhibitor effective to inhibit metastasis of a cancer.

In an embodiment, the Tie-2 inhibitor is rebastinib (4-[4-[(5-tert-butyl-2-quinolin-6-ylpyrazol-3-yl)carbamoylamino]-3-fluorophenoxy]-N-methylpyridine-2-carboxamide).

In an embodiment, the cancer is a breast cancer.

In an embodiment, the breast cancer is an adenocarcinoma.

In an embodiment, the breast cancer is Human Epidermal Growth Factor 2 Negative.

In an embodiment, the breast cancer is a recurrent breast carcinoma.

In an embodiment, the breast cancer is a Stage IV breast cancer.

In an embodiment of the methods, the patient is a human patient.

A metastasis is the existence or development, in a subject with a primary site of cancer, of one or more secondary malignant growths at a distance from the primary site of cancer.

Reducing chemotherapy-induced metastasis means impairing the development of, or reducing the extent of, chemotherapy-induced metastasis (metastasis associated with chemotherapy treatment(s)).

A cancer cell dissemination is the movement of one or more cancer cells away from the site of the cancer.

Reducing chemotherapy-induced cancer cell dissemination means impairing the development of, or reducing the extent of, chemotherapy-induced cancer cell dissemination (cancer cell dissemination associated with chemotherapy treatment(s)).

As used herein a "tumor" is a detectable malignant tumor usually presenting as a lesion or lump located in an organ or tissue in a subject, or in adjacent organs and or tissues in a subject.

In an embodiment, the composition is a pharmaceutical composition. In an embodiment, the pharmaceutical composition comprises a pharmaceutically acceptable carrier. As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

A method for identifying a subject as likely having a poor long-term response to chemotherapy comprising determining, in a sample obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a poor long-term response to chemotherapy wherein a subject is identified as likely having a poor long-term response to chemotherapy when the sample obtained from the subject has a level of Mena$^{Calc}$, Mena$^{INV}$ or TMEM score above the predetermined control level of Mena$^{Calc}$, Mena$^{INV}$ or TMEM score, respectively. In an embodiment, a poor long-term response to chemotherapy means the subject will experience distant recurrence of disease subsequent to the chemotherapy. In an embodiment chemotherapy as used in regard to this method means a cytotoxic chemotherapy in clinical use including taxanes (e.g. paclitaxel), non-taxane microtubule inhibitors (e.g. eribulin), topoisomerase inhibitors (e.g. etoposide), intercalating agents (e.g. doxorubicin), DNA cross-linking agents (e.g. cisplatin), alkylating agents (e.g. cyclophosphamide) or combinations of these. In an embodiment, the sample is a tumor sample. Mena$^{Calc}$ is calculated as total amount of Mena minus total amount of Mena11a in a region of interest or a sample.

A method for identifying a subject as likely having a tumor resistant to a receptor tyrosine kinase (RTK) inhibitor therapy comprising determining, in a sample of the tumor obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a tumor resistant to RTK inhibitor therapy, wherein a subject is identified as likely having a tumor resistant to RTK inhibitor therapy when the sample obtained from the subject has a level of Mena$^{Calc}$, Mena$^{INV}$ or TMEM score above the predetermined control level of Mena$^{Calc}$, Mena$^{INV}$ or TMEM score, respectively. In an embodiment, the RTK inhibitor therapy comprises a EGFR, HGFR, IGFR, CSF1R, VEGFR or TK (Src, Abl, Arg) inhibitor. In an embodiment, resistance is dissemination of tumor cells to distant sites in the presence of the RTK inhibitor. This resistance may be associated with distant metastasis at a later time.

A method for identifying a subject as likely having a tumor resistant to a receptor tyrosine kinase (RTK) inhibitor and cytotoxic chemotherapy combination therapy comprising determining, in a sample of the tumor obtained from the subject, the level of Mena$^{Calc}$, Mena$^{INV}$ or a TMEM score thereof, and comparing to a predetermined control level of Mena$^{Calc}$, Mena$^{INV}$ or TMEM score, respectively, and identifying the subject as having a tumor resistant to RTK inhibitor and cytotoxic chemotherapy combination therapy, wherein a subject is identified as likely having a tumor resistant to RTK inhibitor therapy and cytotoxic chemotherapy combination therapy when the sample obtained from the subject has a level of Mena$^{Calc}$, Mena$^{INV}$ or TMEM score above the predetermined control level of Mena$^{Calc}$, Mena$^{INV}$ or TMEM score, respectively. In an embodiment, the resistance is dissemination of cancer cells to distant sites and/or lack of decrease in tumor size and/or continuous tumor growth at primary and distant sites in presence of the drugs. This resistance may be associated with distant metastasis at a later time.

Mena$^{INV}$ expression in tumor cells resulting from macrophage contact increases sensitivity of RTKs (EGFR, HGFR, IGFR, CSF1R) to their ligands and resistance of tumor cells to RTK (EGFR, HGFR, IGFR, CSF1R, Tie2, VEGFR) and TK (Src, Abl, Arg) inhibitors. Resistance is defined as continued signaling to ligands of these RTKs and upstream pathway signals to TKs resulting in cancer cell dissemination to distant sites and lack of growth inhibition and/or continued growth at primary and distant sites. This resistance may be associated with distant metastasis at a later time. Resistance here is applicable to estrogen and/or progesterone hormone receptor positive, Her2/Neu positive and triple negative subtypes of breast cancer. Resistance as used herein is applicable to all stages of invasive disease; i.e. localized breast cancer (stages I-III) and metastatic disease (stage IV), as well as carcinoma in situ.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

The inventors hypothesized that preoperative chemotherapy might increase the density and the activity of TMEM sites as well as expression of invasion promoting Mena isoforms within the primary tumor and consequently induce cancer cell dissemination and distant metastasis while at the same time reducing cancer burden. Such a side effect would diminish the clinical benefit of NAC. If this was the case, it might also be possible that this effect could be blocked by inhibitors of TMEM function. Herein, the inventors tested this hypothesis by using fixed tissue and intravital imaging of PyMT murine models and patient-derived xenografts, as well as pre- and post-NAC (paclitaxel followed by doxorubicin plus cyclophosphamide) breast cancer tissue samples from human patients.

Results

Paclitaxel Delays Tumor Growth but Increases TMEM Assembly in Breast Cancer: Chemotherapy induces recruitment of endothelial progenitors and Tie2$^+$ monocyte progenitors into the tumor (10, 11, 30), and this laboratory has previously demonstrated that Tie2$^{hi}$ macrophages are required for TMEM-mediated cancer cell intravasation (1). Herein, the possibility was examined that neoadjuvant paclitaxel promotes TMEM assembly and cancer cell dissemination and metastasis. This hypothesis was investigated in the following breast carcinoma models: (i) transgenic MMTV-PyMT mice bearing spontaneous breast tumors, (ii) FVB mice transplanted orthotopically with tumors from MMTV-PyMT donors, and (iii) two patient-derived xenografts (PDX), HT17 and HT33, developed previously in our laboratory (31). Animals were treated with 10 mg/Kg paclitaxel every five days, three times in total, as shown in FIG. 1A, and upon sacrifice, tumor growth, Tie2 macrophage recruitment and TMEM assembly were evaluated. Treatment of all groups began at the early carcinoma stage (tumor size of ~0.3 cm) when there is minimal or absent necrosis. It was decided to work with the early-stage PyMT mouse mammary carcinoma model because it more accurately reflects clinically relevant scenarios where most women present with small tumors of <2 cm (32). At the end of treatment all tumors were histologically classified as invasive carcinomas. Although paclitaxel-treated tumors showed delayed tumor growth, they revealed 2- to 3-fold higher TMEM score (p<0.001) compared to non-treated controls in all the experimental models tested (FIG. 1).

Figures 1C, 1D, 1E, 1F:
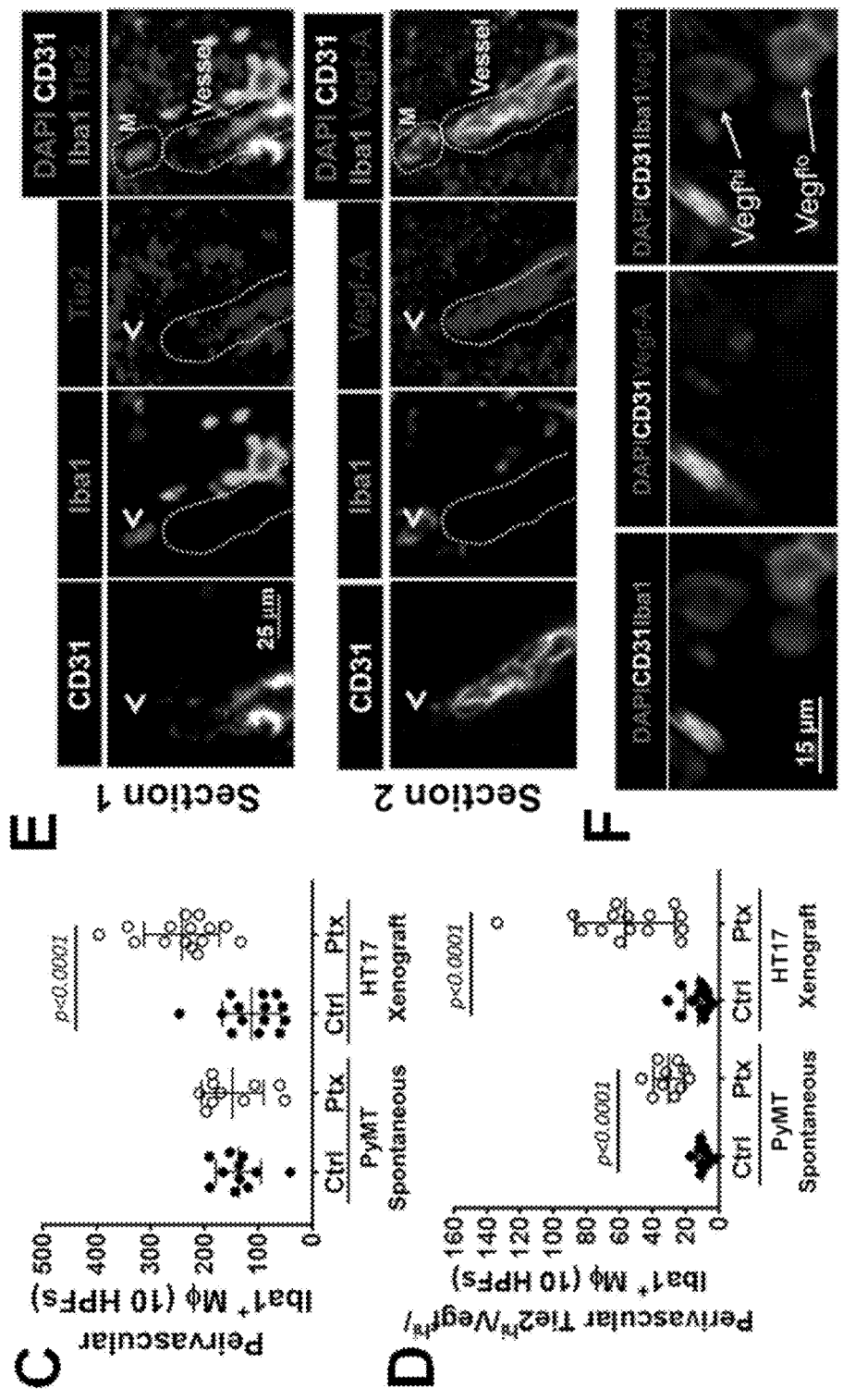

Paclitaxel Increases the Infiltration of Perivascular Tie2$^{hi}$/Vegf$^{hi}$ Macrophages in the Primary Breast Cancer Microenvironment—To explain the mechanism of increased TMEM assembly upon administering chemotherapy in breast tumors, we investigated if paclitaxel affects intratumoral macrophage density, as previously suggested (33). A significant increase (p<0.01) was found in the percentage of macrophage-specific Iba1+ area in paclitaxel-treated mice in all transplantation models, except in the PyMT-spontaneous model. The absolute number of Iba1+ cells was also significantly increased (p<0.001) in the paclitaxel-treated HT17-xenograft but not in the PyMT-spontaneous model, when quantified either over the entire tissue, or only in the perivascular niche, where TMEM structures are located (FIG. 1C).

The functional TMEM sites contain $Tie2^{hi}/Vegf^{hi}$ macrophages and invasive tumor cells in perivascular regions (1), and it was independently shown that chemotherapy may promote mobilization of such $Tie2^{hi}$ monocyte progenitors in primary tumors (8, 10). The $Tie2^{hi}/Vegf^{hi}$ macrophage subpopulation was quantified herein using multi-channel immunofluorescence (IF) imaging (FIGS. 1D-F) (10, 14, 34). FIG. 1E illustrates a representative IF image of a $Tie2^{hi}/Vegf^{hi}$ macrophage quantified using Cd31, Iba1, Vegf and Tie2 staining. FIG. 1F illustrates representative examples of $Vegf^{hi}$ and $Vegh^{lo}$ macrophages as seen comparatively in the same fields of view, by combining Cd31, Iba1 and Vegf staining. Upon quantification, paclitaxel-treated mice had significantly higher (p<0.001) density of $Tie2^{hi}/Vegf^{hi}$ macrophages compared to the vehicle-treated controls, regardless of whether these were assessed in the entire tissue or only in the perivascular niches (FIG. 1D). The proportion of $Tie2^{hi}/Vegf^{hi}$ macrophages among all Iba1+ cells was also increased by paclitaxel treatment. Importantly, the significant increase of the perivascular $Tie2^{hi}/Vegf^{hi}$ macrophage subpopulation was also demonstrated in the PyMT-spontaneous model (FIG. 1D), indicating a significant change in macrophage population dynamics in preference of Tie2+ upon paclitaxel treatment.

Figures 1G, 1H:
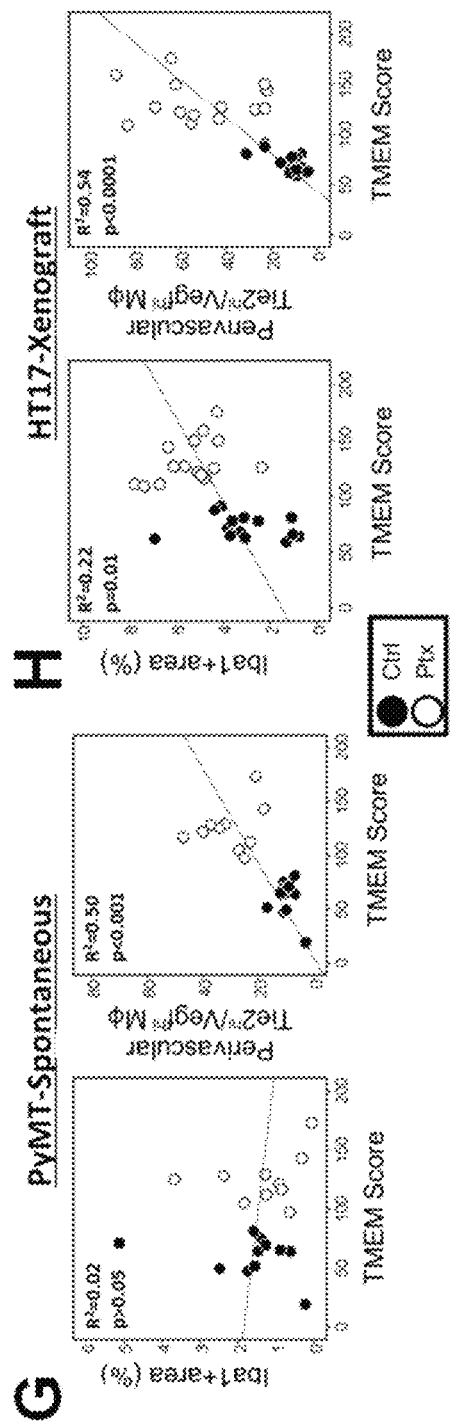

In the PyMT-spontaneous model, the total Iba1+ macrophage counts correlated very poorly with TMEM score (FIG. 1G, left panel), but we found comparatively stronger correlations (p<0.001) of TMEM with perivascular $Tie2^{hi}/Vegf^{hi}$ macrophages ($R^2$=0.5) (FIG. 1G, right panel). In the HT17-xenograft, both total Iba1+ macrophages (FIG. 1H, left panel) and perivascular $Tie2^{hi}/Vegf^{hi}$ macrophages (FIG. 1H, right panel) correlated equally well ($R^2$=0.65 and $R^2$=0.55, respectively) with TMEM score (p<0.001, in both cases). Both TMEM score values and perivascular $Tie2^{hi}/Vegf^{hi}$ macrophages remained significantly increased upon chemotherapy treatment, even after their values were normalized to microvascular density. Collectively, these data indicate that at least in the case of PyMT-spontaneous tumors, the increased TMEM assembly after paclitaxel treatment does not necessarily occur due to random spatial juxtaposition of tumor-associated vasculature with infiltrating macrophages, but is specifically associated with the recruitment of $Tie2^{hi}/Vegf^{hi}$ macrophages in the perivascular niche. In conclusion, neoadjuvant paclitaxel specifically promotes the assembly of TMEM sites containing the $Tie2^{hi}/Vegf^{hi}$ macrophage that is required for TMEM activity in primary breast cancer.

Figures 2A, 2B:
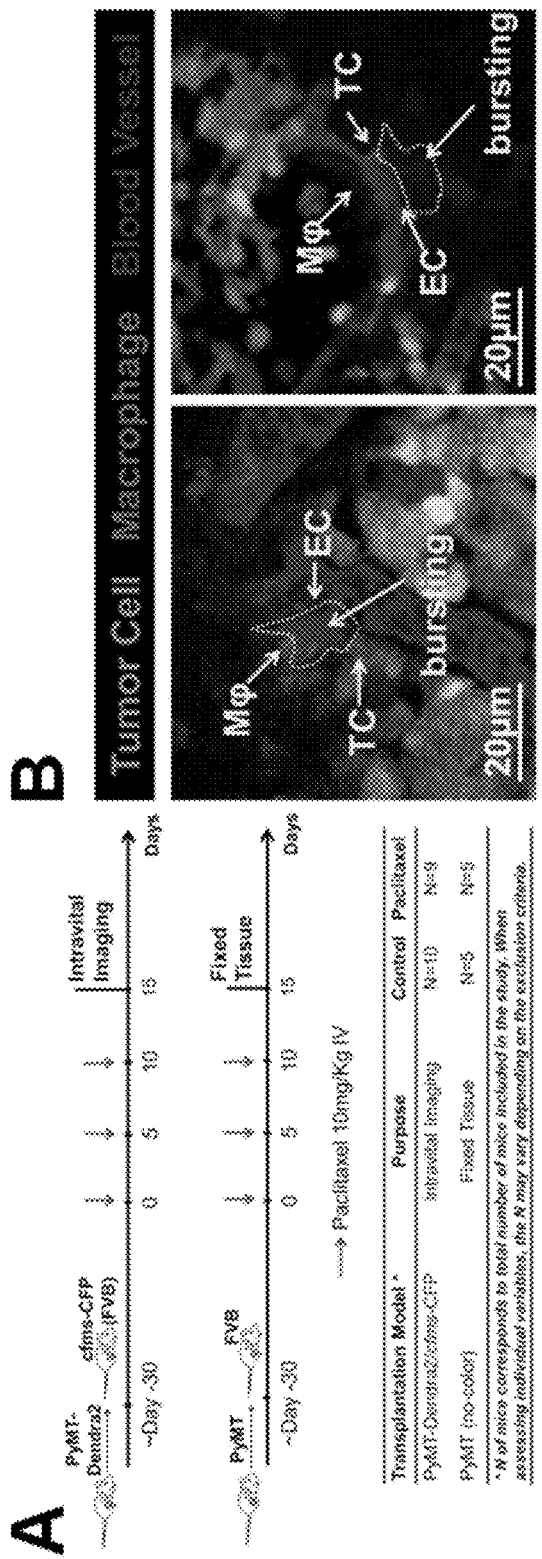
FIG. 2A-2F. Paclitaxel Induces Vascular Permeability Exclusively at TMEM Sites: (A) Experimental design and cohort composition. (B) Two examples of images taken from a cfms-CFP mouse grafted with MMTV-PyMT/Dendra2$^+$ tumor. Bursting at TMEM (TMEM activity) identified by the presence of tetramethylrhodamine (TMR)-conjugated 155 kDa Dextran in the extravascular space (left image). Outline of the burst is indicated by dotted yellow line. Right image demonstrates absence of bursting at TMEM, as a control. Mφ, macrophage; TC, tumor cell; EC, endothelial cell. (C) Left; regions of interest (ROI) selection for calculation of Dendra2/TMR signal intensity over time. Right; the quantification of extravascular dextran (red lines) and dendra2-labeled intravasating cancer cell (green lines) signal intensity in the selected TMEM-associated (straight lines) or away from TMEM (dotted lines) ROIs from the image on the left. (D) Normalized fluorescence intensity of Dextran-TMR, averaged from all bursting sites. (E) IF of endomucin (first column), Dextran-TMR (second column), their merged image (third column), the corresponding thresholded blood vessel and extravascular dextran masks (fourth column) and the corresponding sequential section of TMEM IHC (fifth column) in MMTV-PyMT mice treated with paclitaxel. Upper row, TMEM-associated vascular profile; lower row, vascular profile away from TMEM. (F) Percentage of vascular profiles with extravascular dextran that have at least one TMEM site or no TMEM sites associated with them for vehicle-treated (left graph) or paclitaxel-treated (right graph) cases.
Figures 2C, 2D, 2F:
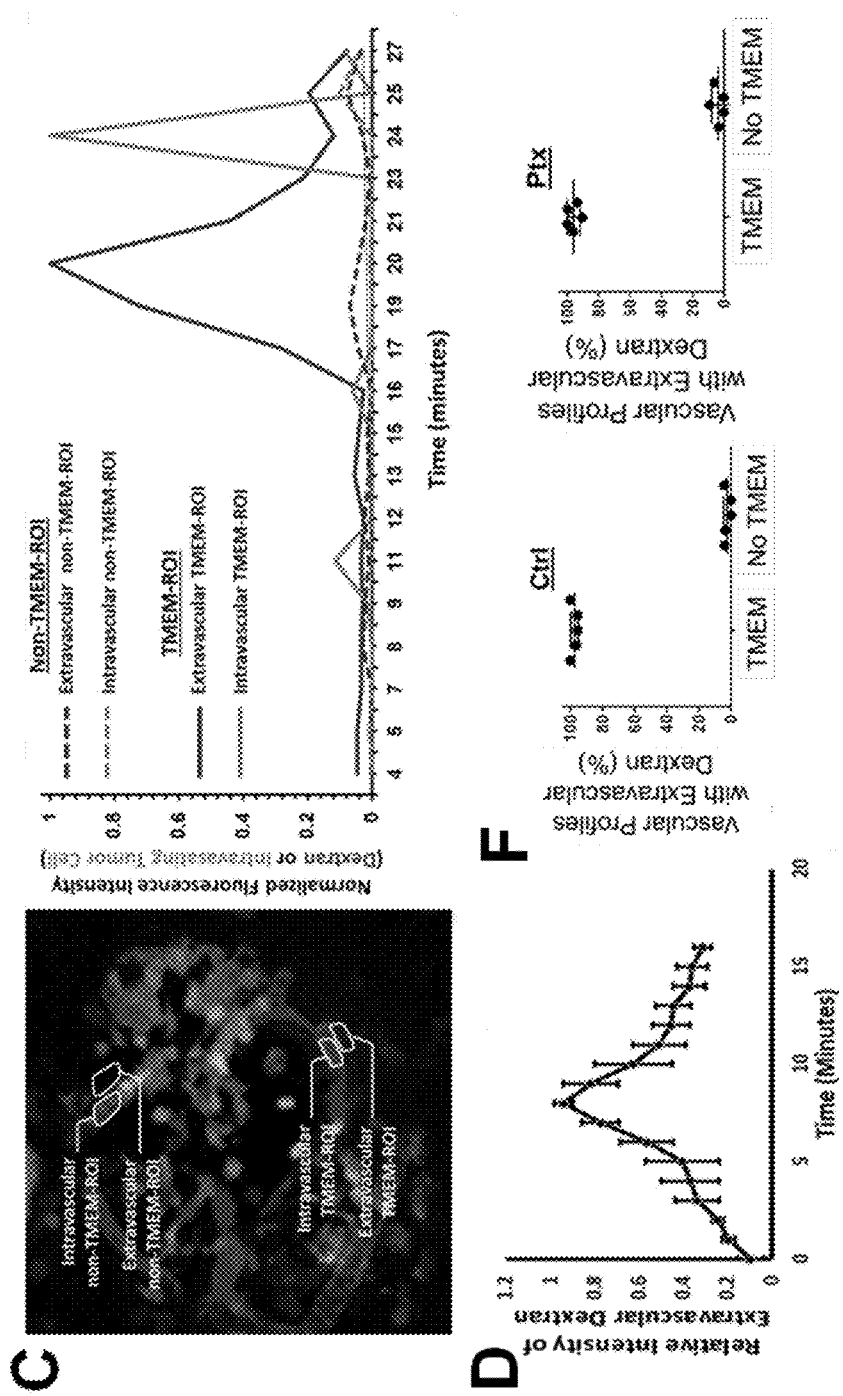

Paclitaxel Induces TMEM-Dependent Vascular Permeability in Breast Tumors—Given that chemotherapy treatment may affect blood vessel dynamics by inducing angiogenesis (9, 11-13, 35-37), intravital imaging (IVI) (FIG. 2A) was used to investigate whether neoadjuvant paclitaxel induces TMEM-dependent (localized) or TMEM-independent (more universal) blood vessel leakage. Tumors in mice treated with paclitaxel did not demonstrate generalized blood vessel leakage of 155-KDa dextran into the extravascular space. Instead, they showed localized areas of transient vascular permeability called "bursting" (FIG. 2B, similar to those observed previously in untreated tumors (1). In particular, FIG. 2B illustrates a characteristic example of peak bursting activity (still image on the left of FIG. 2B) on a TMEM site, though not all TMEM presented with bursting activity (still image on the right of FIG. 2B); bursting was not captured for all observed TMEM sites. Importantly, all the "bursting" incidents occurred only at TMEM sites, i.e. in close proximity to at least one Dendra2+ tumor cell and one CFP+ macrophage (FIG. 2B, left image). As also reported previously (1), we never observed any bursting incidents without juxtaposition to a clearly defined TMEM site. Bursting was documented by the accumulation of Dextran-TMR signal over time around an active TMEM site, and no such accumulation was observed away from TMEM (FIGS. 2B-C). The entire time-lapse of these was recorded in videos, respectively. The intensity values from all TMEM-mediated bursting incidents observed in paclitaxel-treated mice were averaged and plotted over the entire time of bursting activity (FIG. 2D), which confirmed the transient nature of paclitaxel-induced TMEM-dependent vascular permeability. In conclusion, chemotherapy treatment in early-stage PyMT tumors was able to recapitulate bursting similar to the one observed in untreated, late-stage PyMT tumors (1).

To explicitly demonstrate that tumor cell intravasation after paclitaxel treatment is dependent on TMEM-dependent bursting, we measured the tumor cell-specific Dendra2 signal intensity in blood vessel ROIs that were directly juxtaposed to or away from bursting (FIG. 2C). Signal intensity of Dextran-TMR was also quantified in the corresponding extravascular ROIs for purposes of confirming the presence of bursting. It was found that cancer cell intravasation in paclitaxel-treated animals occurs during or shortly after the bursting event, specifically at TMEM sites associated with bursting, but never before the bursting event, or at the TMEM sites without bursting activity (FIG. 2C).

Figure 2E:
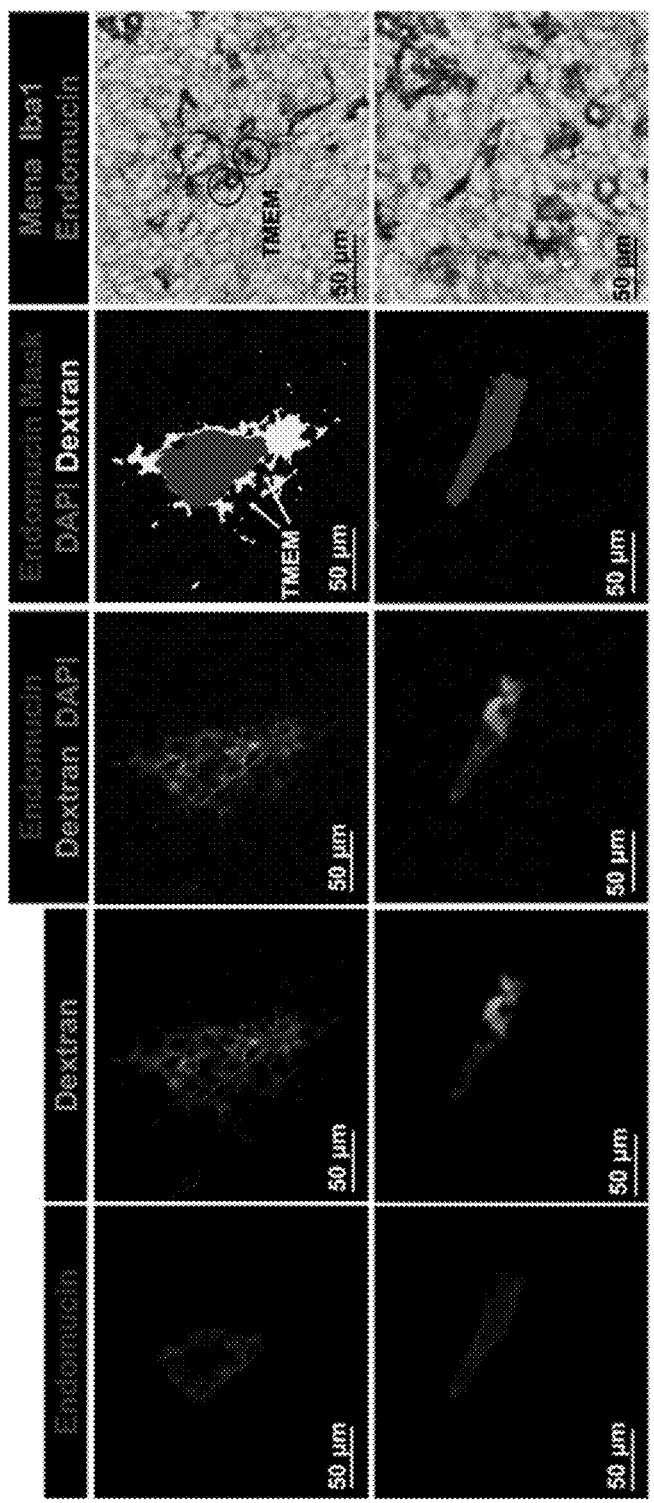

In a second independent validation experiment, a group of vehicle- or paclitaxel-treated mice received an i.v injection of Dextran-TMR for 1 hour and then sacrificed and evaluated for vascular permeability in fixed tumor sections (FIG. 2A). Multichannel IF staining included endomucin as a blood vessel exclusion mask and a specific anti-TMR antibody for assessing dextran leakage. A corresponding TMEM IHC staining section was co-aligned to evaluate the presence/absence of TMEM in each vascular profile that presented with vascular leakage. Two examples of vascular profiles selected from a paclitaxel-treated mouse are demonstrated in FIG. 2E; the upper row shows a vascular profile with abundant extravascular dextran which co-localized with 2 TMEM sites, while the lower row shows a vascular profile with absent or minimal extravascular dextran which co-localized with a blood vessel lacking TMEM (FIG. 2E). For quantification purposes, ~20-30 vascular profiles were selected for each mouse, based on tissue size, degree of vascularization and quality of endomucin staining. In both vehicle-treated and paclitaxel-treated groups, approximately 96-98% of the vascular profiles with extravascular dextran co-localized with at least 1 TMEM (FIG. 2F).

Figure 3A:
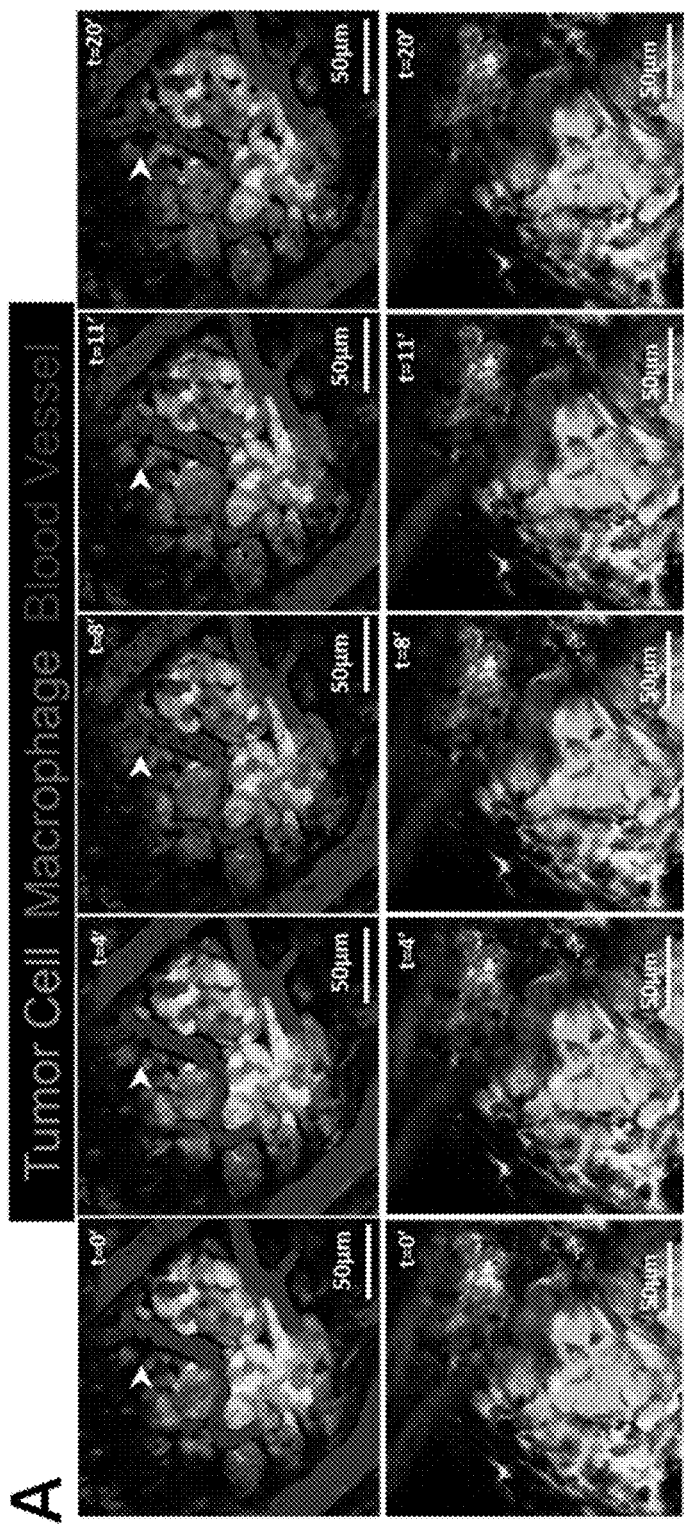
Figure 3E:
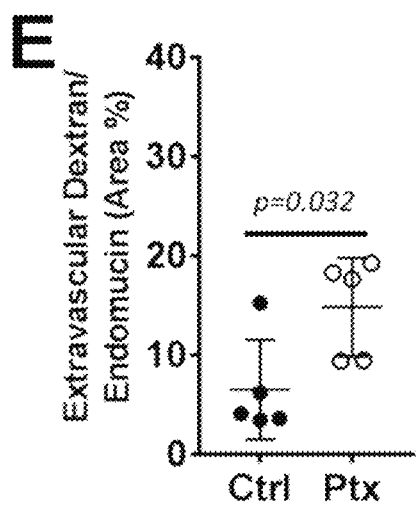

Paclitaxel Increases Metastatic Dissemination of Breast Tumors—To assess if paclitaxel treatment promotes tumor cell dissemination and metastatic incidence, we first quantified and compared incidence and frequency of bursting in mice treated with vehicle or paclitaxel, using IVI (FIGS. 3A-C). The incidence (at least 1 bursting event in a ~4.5-hour imaging session) and frequency of bursting were increased in mice treated with paclitaxel, when compared to those treated with vehicle control (FIGS. 3B-C). The same conclusions were reached when frequency of bursting was normalized to the number of TMEM sites, as measured in each field. Unlike in late-stage tumors in which TMEM show spontaneous activity, TMEM-associated bursting is a very rare phenomenon in early carcinoma (FIG. 3C) as we have already reported (1). However, TMEM-associated bursting can be induced by chemotherapy. In addition to IVI, extravascular dextran area was quantified and compared as % normalized to the blood vessel area in fixed tumors of mice treated with either vehicle or paclitaxel, using multichannel IF. Extravascular dextran was 3-fold ($p<0.05$) more abundant in paclitaxel-treated compared to vehicle-treated mice (FIGS. 3D-E). Since we have demonstrated that bursting (as visualized through IVI) and extravascular dextran (as quantified in fixed-tissue IF), are both associated with TMEM (FIG. 2), the data presented in FIGS. 3A-E collectively demonstrate that paclitaxel-treated tumors have increased TMEM-mediated vascular permeability compared to non-treated controls.

Figure 3F:
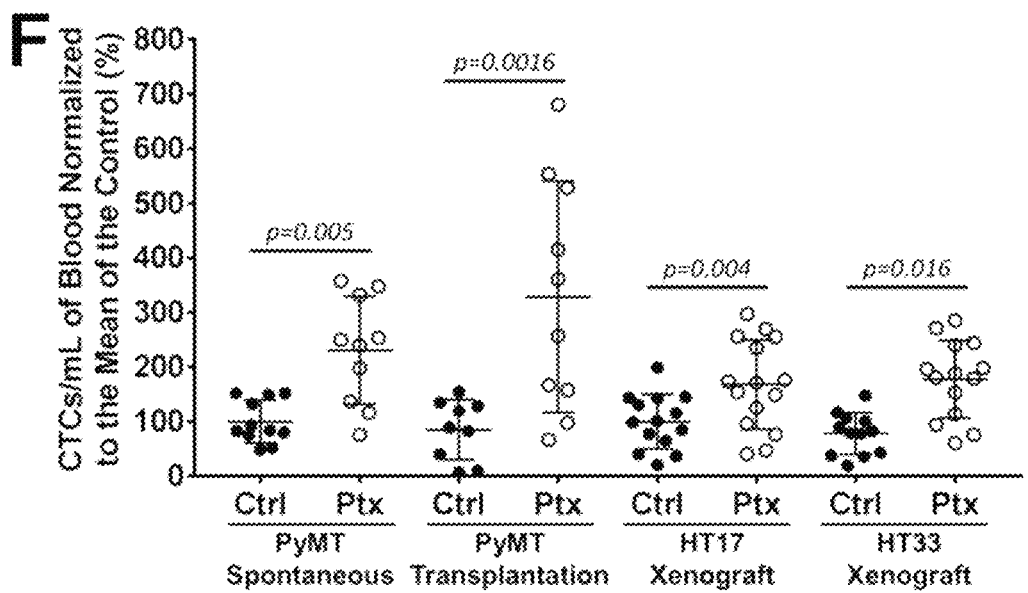
Figures 3G, 3H, 3I, 3J:
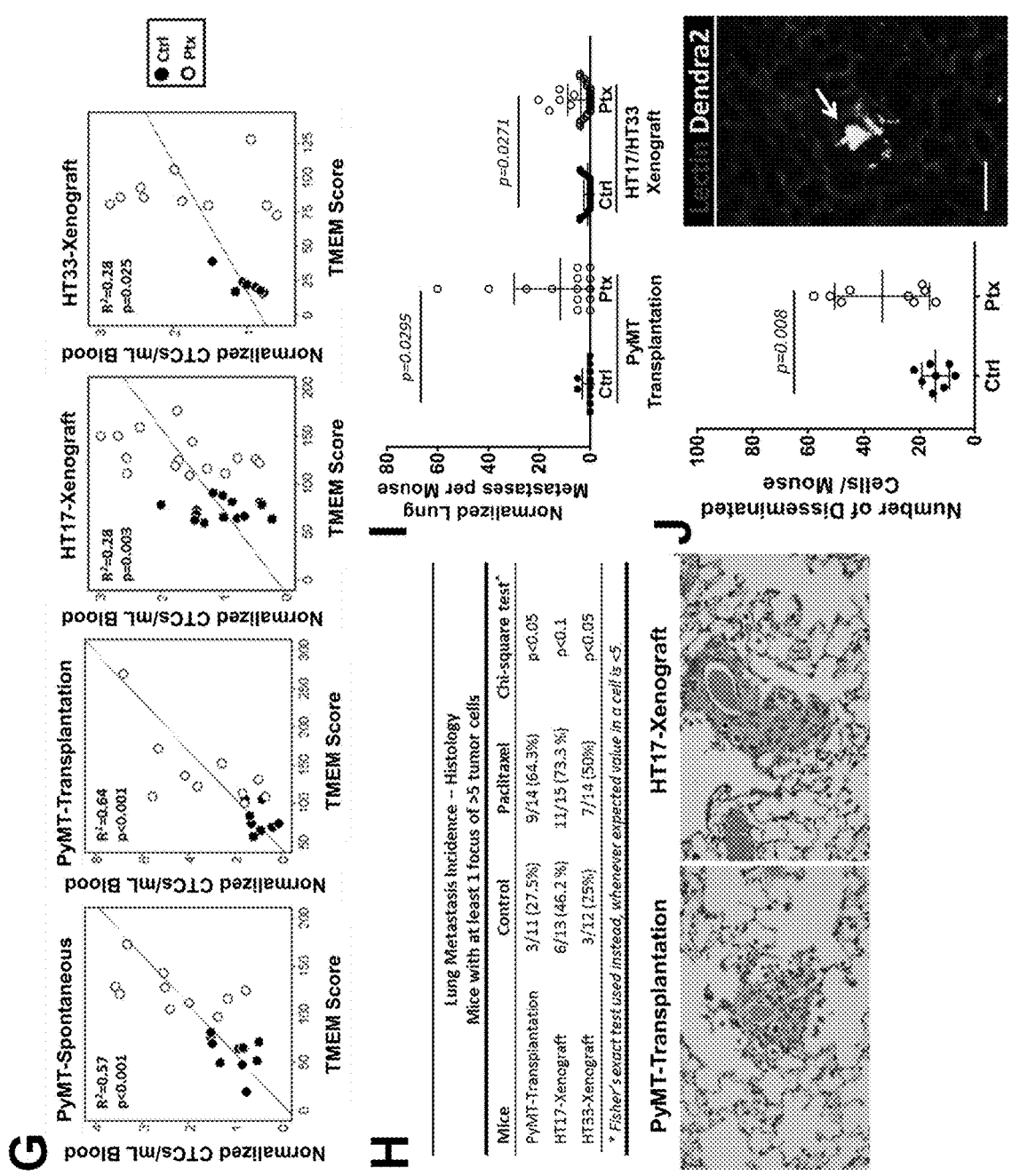

Having shown that TMEM function is additionally associated with tumor-cell intravasation in chemotherapy-treated tumors (FIG. 2C) as in the case of non-treated tumors (1), it was then asked whether paclitaxel treatment induces increased metastatic dissemination of breast cancer cells. An at least 2-fold increase was found in circulating tumor cells (CTCs) ($p<0.05$) following paclitaxel treatment in all experimental models examined (FIG. 3F). TMEM score and CTCs correlated positively in the PyMT-spontaneous ($R^2=0.57$, $p<0.001$), the PyMT-transplantation ($R^2=0.63$, $p<0.001$), as well as in both patient-derived xenograft (PDX) models, the HT17 ($R^2=0.28$, $p<0.05$) and the HT33 ($R^2=0.28$, $p<0.05$), though correlations were weaker in the latter models (FIG. 3G). Since SCID mice used in the latter models are engineered to lose their adaptive but to retain their innate immunity, it is possible that the weaker correlations were due to a differential degree of immune-mediated rejection of CTCs.

To further determine the effect of paclitaxel on cancer cell dissemination to distant sites, we harvested lungs and evaluated metastatic foci histologically. An increase was found in both the metastatic incidence (>1 micrometastatic focus of >5 tumor cells) (FIG. 3H) and the number of cancer cell micrometastases in the lungs of paclitaxel-treated mice (FIG. 3I). In addition, we quantified single cell dissemination of breast cancer cells in the lungs of FVB-recipient mice after syngeneic transplantation of MMTV-PyMT/Dendra2$^+$ tumors using ex vivo microscopy, and found an approximately 2-fold increase ($p<0.01$) of single Dendra2$^+$ breast cancer cells in the lungs of paclitaxel-treated mice (FIG. 3J). Overall, data presented in this section indicate that in early-stage breast cancers chemotherapy increases vascular permeability at TMEM sites which is accompanied by increased cancer cell dissemination.

Figures 4A, 4B, 4C, 4D:
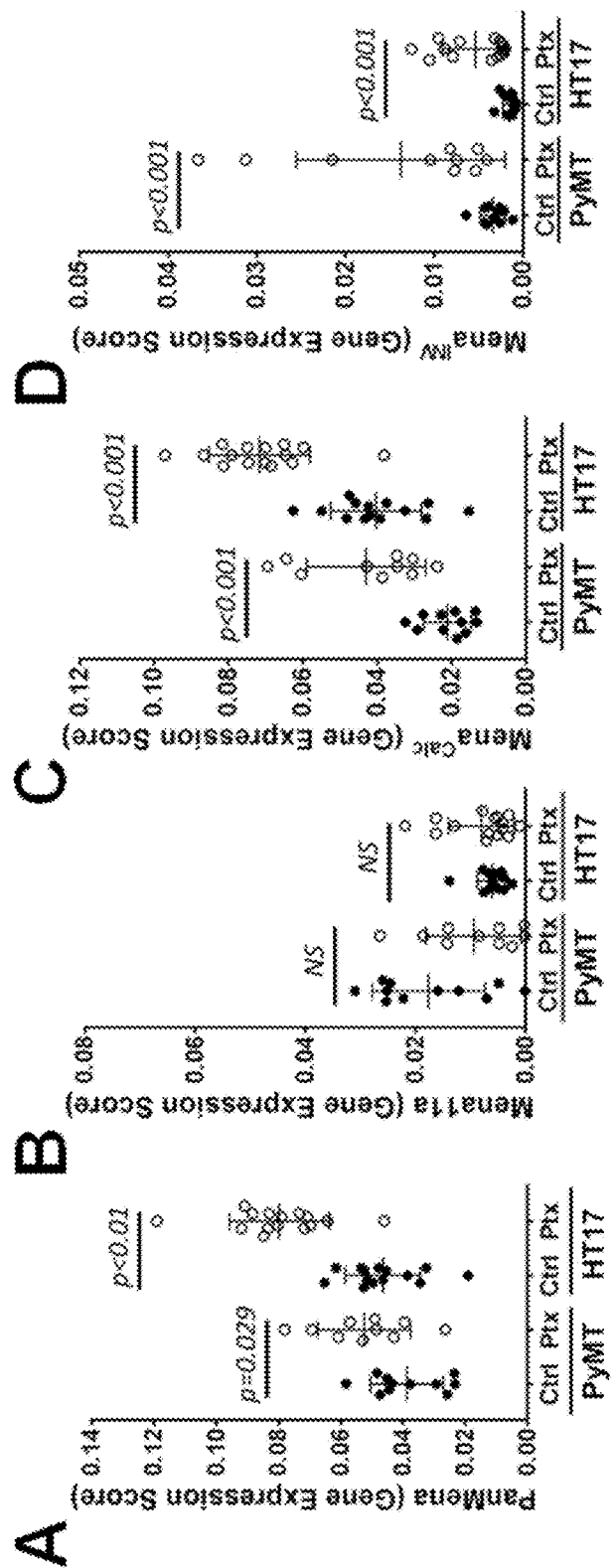
FIG. 4A-4G. Paclitaxel Promotes the Expression of Invasive Isoforms of Mena in the Primary Breast Cancer Microenvironment. (A-D) Gene-expression levels of Mena or Mena isoforms (real-time RT-PCR) following RNA extraction from formalin-fixed paraffin-embedded (FFPE) tumors. Gene expression levels of Pan-Mena (A), Mena11a (B), Mena$^{Calc}$ (C) and Mena$^{INV}$ (D) indicated. Mann-Whitney U-test. (E) Correlations of Mena$^{calc}$ with TMEM and Mena$^{INV}$ gene-expression with TMEM in the PyMT-spontaneous and HT17-xenograft tumors ($R^2$=Pearson's Coefficient of Determination). Filled circles, control; open circles, paclitaxel. (F) Mena$^{INV}$ protein expression visualized by Mena$^{INV}$ immunofluorescence and DAPI in PyMT-spontaneous and HT17-xenograft tumors, treated with paclitaxel or vehicle control. (G) Quantification of the Mena$^{INV}$-positive area (%) in tumors shown in F. Mann-Whitney U-test.
Figures 4E, 4F, 4G:
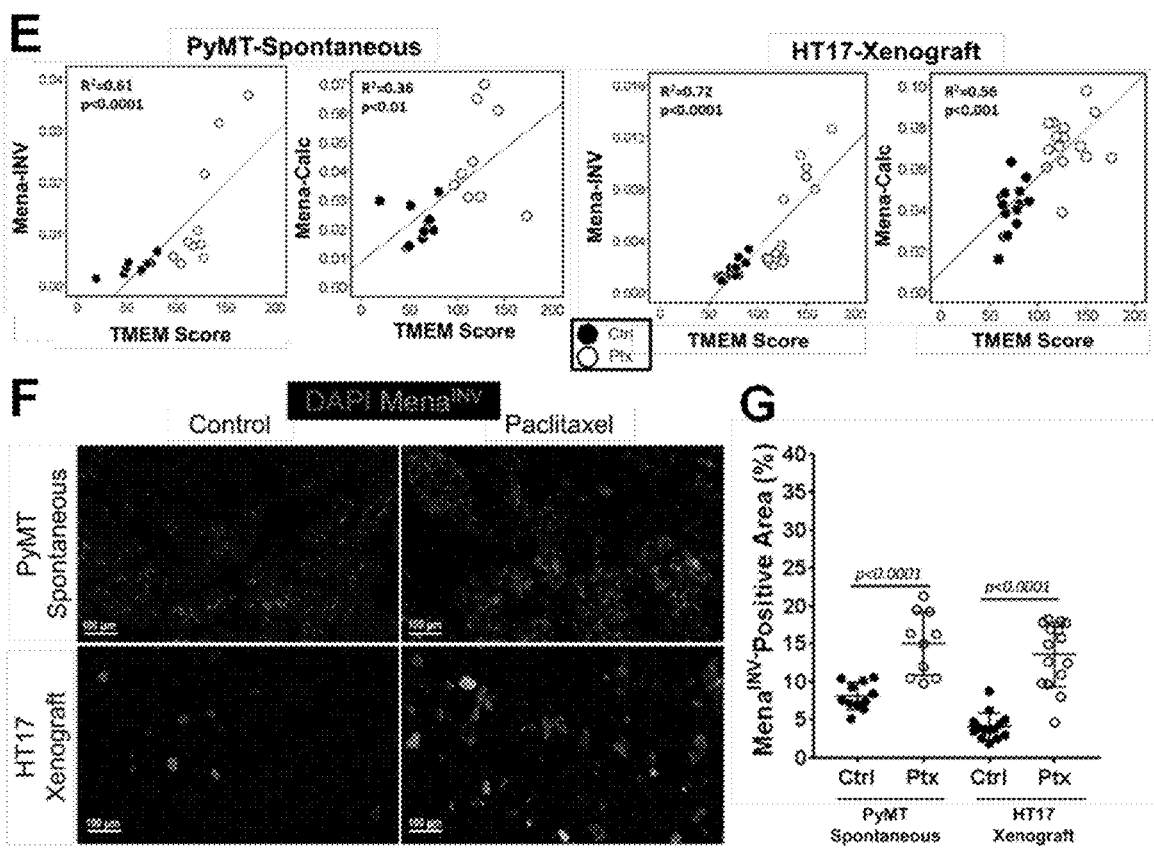

Paclitaxel Promotes the Expression of Invasive Isoforms of Mena in Breast Tumors—Since the data show that paclitaxel treatment increases TMEM assembly, as well as TMEM-dependent vascular permeability and metastatic dissemination, we hypothesized that it also increases the proportion of highly migratory cancer cells, known to express invasive isoforms of the actin-regulatory protein Mena (20, 22), capable of assembling and using TMEM sites to intravasate, which is one of the major prerequisites for successful metastatic seeding. To test this hypothesis, qRT-PCR analysis was first performed for total Mena (panMena), Mena11a and Mena$^{INV}$ on formalin-fixed paraffin-embedded (FFPE) tumors from all mouse models. Paclitaxel treatment significantly increased ($p<0.01$) the expression of PanMena (defined as all Mena isoforms), Mena$^{INV}$, and Mena$^{Calc}$, a marker that takes into account the full repertoire of invasive Mena isoforms including Mena$^{INV}$ (38, 39), but not that of the anti-metastatic Mena11a (FIG. 4A-D), and correlates with distant recurrence in breast patients (38, 39). In addition, both Mena$^{Calc}$ and Mena$^{INV}$ correlated positively with increased TMEM score (Mena$^{INV}$, $p<0.001$; Mena$^{Calc}$, $p<0.01$) in both models tested (FIG. 4E), with Mena$^{INV}$ demonstrating higher correlation coefficients than Mena$^{Calc}$ (Mena$^{Calc}$ 0.36 versus Mena$^{INV}$ 0.61 for PyMT-spontaneous, and Mena$^{Calc}$ 0.56 versus Mena$^{INV}$ 0.72 for HT17-xenograft). Paclitaxel-mediated Mena$^{INV}$ increased expression ($p<0.0001$) and correlation with TMEM score ($p<0.001$) were also confirmed at the protein level in both the PyMT-spontaneous and the HT17-xenograft models (FIGS. 4F-G). As shown in the specific Mena$^{INV}$ IF, the pattern of Mena$^{INV}$ expression in PyMT mice was heterogeneous (FIG. 4F), consistent with previous observations (40). Interestingly, we found a positive correlation between Tie2$^{hi}$/Vegf$^{hi}$ macrophage infiltration and Mena$^{INV}$ expression ($p<0.0001$, $R^2=0.68$), as well as Mena$^{Calc}$ ($p<0.05$, $R^2=0.24$), supporting our recently reported evidence that direct contact of tumor cells with macrophages induces Mena$^{INV}$ expression (27). In addition, there was an inverse correlation for the anti-metastatic Mena11a ($p<0.01$, $R^2=-0.3$).

Figure 5A:
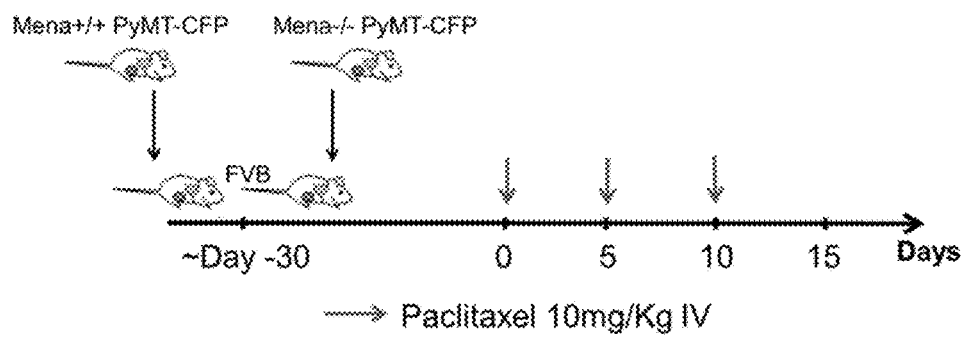
FIG. 5A-5G. Paclitaxel Promotes Breast Cancer Cell Dissemination and Metastasis in a Mena-Dependent Manner. (A) Experimental design and cohort composition. (B) IF of Iba1, Cd31, Vegf and DAPI in a Mena$^{-/-}$ MMTV-PyMT-CFP-transplanted tumor, treated with either paclitaxel (lower panel) or vehicle control (upper panel). Arrowheads; Vegf$^{hi}$/Iba1$^+$ macrophages. (C) Perivascular Iba1$^+$ macrophages counted in 10 HPFs (absolute counts) in Mena–/– MMTV-PyMT-CFP-transplanted tumors treated with paclitaxel or vehicle control. Mann-Whitney U-test. (D-E) Perivascular Tie2$^{hi}$/Vegf$^{hi}$ macrophages quantified in Mena–/– MMTV-PyMT-CFP-transplanted tumors, treated with paclitaxel or vehicle control. Absolute counts (D) or proportion (E) among all perivascular Iba1$^+$ macrophages. Mann-Whitney U-test. (F) CTCs/mL blood collected from Mena$^{+/+}$ and Mena$^{-/-}$ PyMT-CFP mice. Values normalized to the control group in each case to account for inter-cohort variability. Mann-Whitney U-test. (G) Quantification of single cancer cell dissemination in the lungs of Mena$^{+/+}$ and Mena$^{-/-}$ PyMT-CFP transplants, using fluorescent stereomicroscopy. Mann-Whitney U-test. This is the first demonstration that Mena expression and activity is necessary for chemo-induced dissemination and that Mena inhibition will block dissemination. Note that CTC count in FIG. 5F is a direct measure of TMEM activity in this experiment.
Figures 5B, 5C, 5D, 5E:
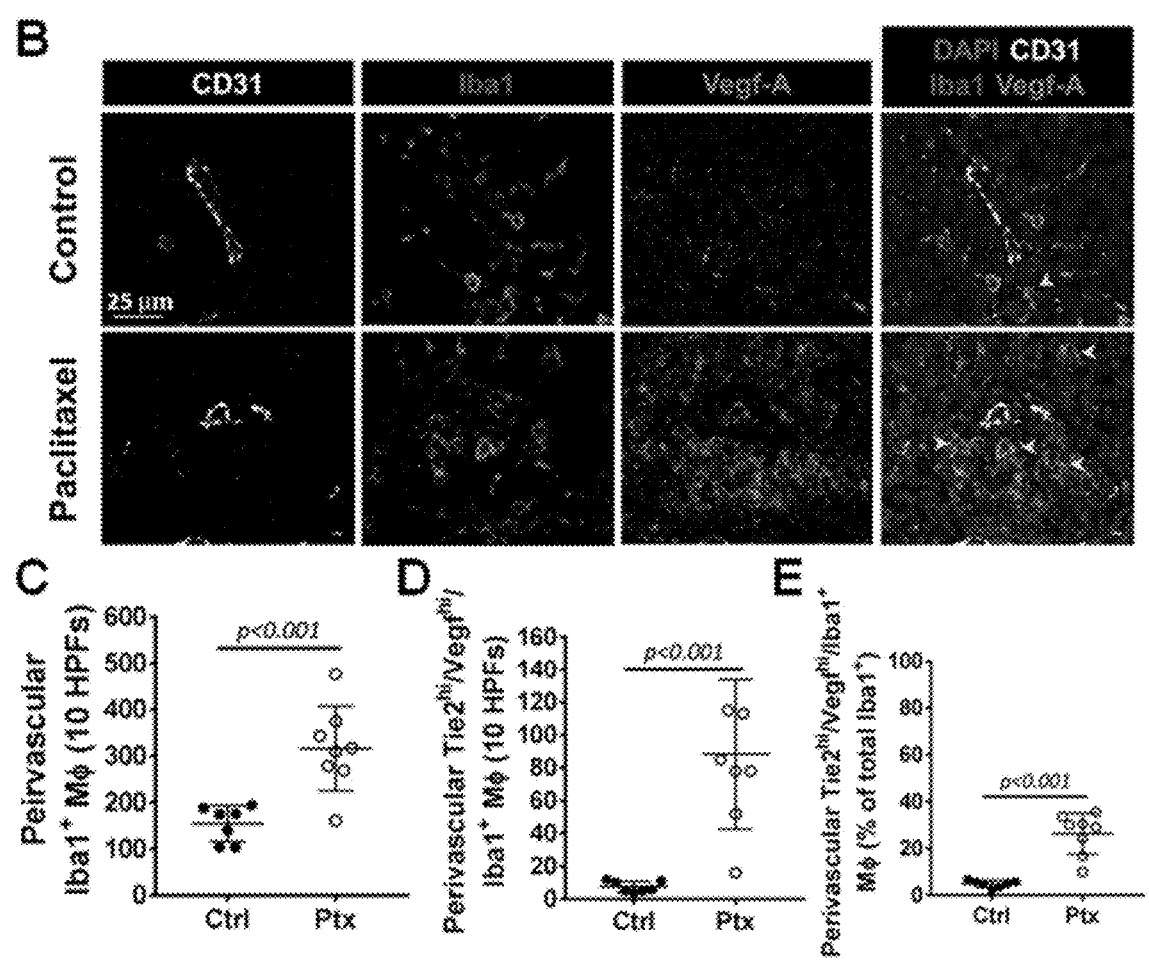

Paclitaxel Promotes Breast Cancer Cell Dissemination in a Mena-Dependent Manner—previous work has demonstrated that animals grafted with MMTV-PyMT Mena-null tumors do not develop circulating tumor cells and lung metastases (28), indicating that Mena is necessary for tumor cell dissemination. Having shown that paclitaxel increases TMEM assembly (FIG. 1B) and invasive Mena isoform expression (FIGS. 4C-D and FIG. 4F-G), we next investigated if paclitaxel-mediated tumor cell dissemination in invasive breast cancer was also Mena-dependent. To test this hypothesis, we orthotopically transplanted Mena$^{-/-}$ or Mena$^{+/+}$ CFP-fluorescent PyMT-tumors into wild-type syngeneic hosts to assess tumor cell intravasation and dissemination in the lungs of mice after paclitaxel treatment (FIG. 5A). Mena$^{-/-}$ mice did not express Mena$^{INV}$ at the protein level. Quantitative assessment of macrophages in the perivascular niches of Mena$^{-/-}$ mice revealed both increased Iba1$^+$ and Tie2$^{hi}$/Vegf$^{hi}$ Iba1$^+$ macrophage infiltration after paclitaxel treatment (FIG. 5B-E), similar to changes observed in PyMT and HT17 Mena$^{+/+}$ mice after receiving chemotherapy (FIG. 1C-D). These results indicate that Mena is not necessary for paclitaxel mediated Tie2$^{hi}$/Vegf$^{hi}$ macrophage recruitment in the primary breast tumor microenvironment (FIG. 5B).

Figures 5F, 5G:
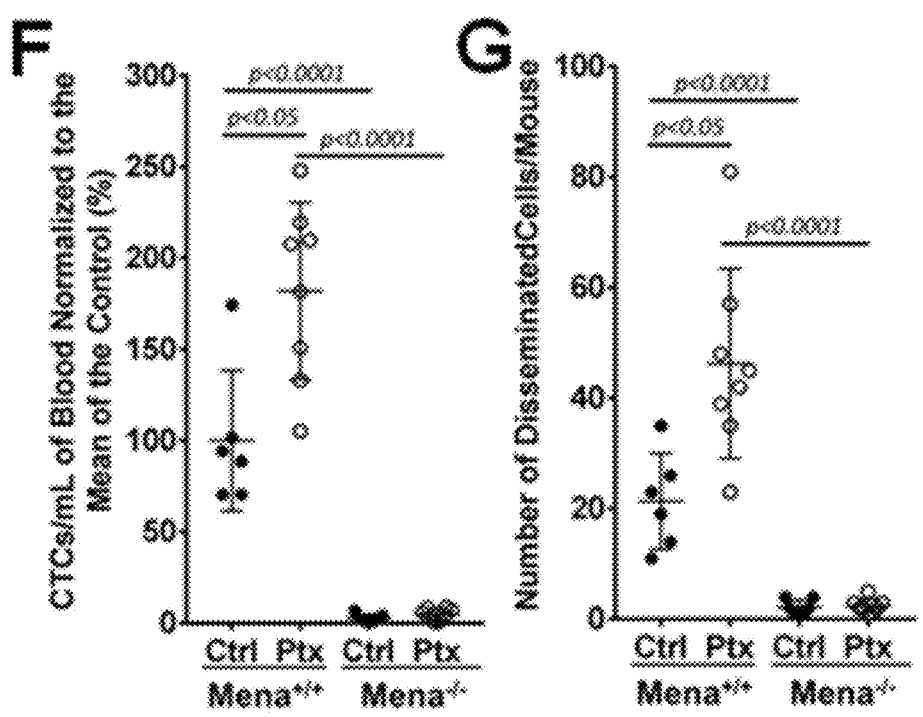

Since a Mena-expressing tumor cell constitutes one of the elements of the tripartite TMEM structure, Mena-null tumors do not assemble TMEM. However, since the perivascular Tie2$^{hi}$/Vegf$^{hi}$ macrophages could be recruited by paclitaxel treatment even in the Mena-null tumors (FIGS. 5D-E), it was next investigated whether these Tie2$^{hi}$/Vegf$^{hi}$ macrophages were by themselves sufficient to cause increased cancer cell dissemination, without the presence of a complete TMEM structure. However, the absence of the Mena gene completely eliminated CTCs ($p<0.0001$) and the number of single cancer cells disseminating in the lungs ($p<0.0001$) (FIG. 5F-G), as has also been previously shown (28). This suppression was consistent regardless of vehicle or paclitaxel treatment (FIGS. 5F-G), indicating that the elimination of the Mena gene in breast cancers affects cancer cell intravasation and dissemination, even though it still permits the paclitaxel-mediated increase of perivascular Tie2$^{hi}$/Vegf$^{hi}$ macrophages. Thus, paclitaxel treatment in Mena$^{-/-}$ PyMT-CFP transplants failed to boost the number of CTCs in the blood or disseminated cells in the lungs, as seen in the case of Mena$^{+/+}$ mice (FIGS. 5F-G). In summary, these data show that paclitaxel-induced tumor cell dissemination is also dependent on Mena expression, further supporting the essential role of TMEM in paclitaxel tumor cell dissemination. Blocking expression or function of Mena is therefore very valuable therapeutically.

Figure 6A:
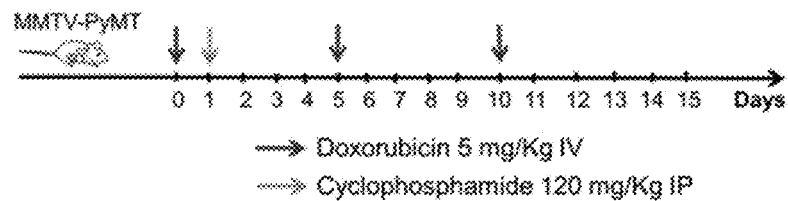
Figure 6B:
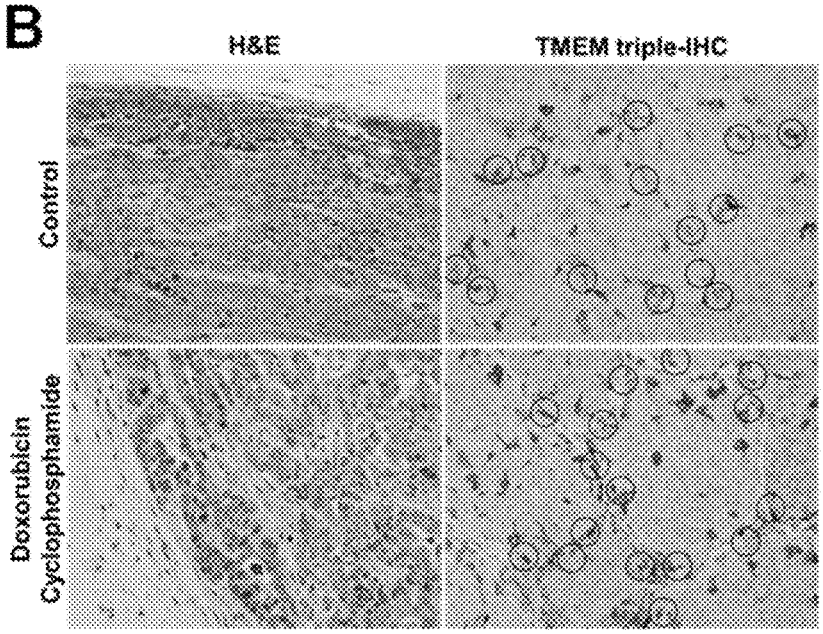
Figures 6C, 6D, 6E:
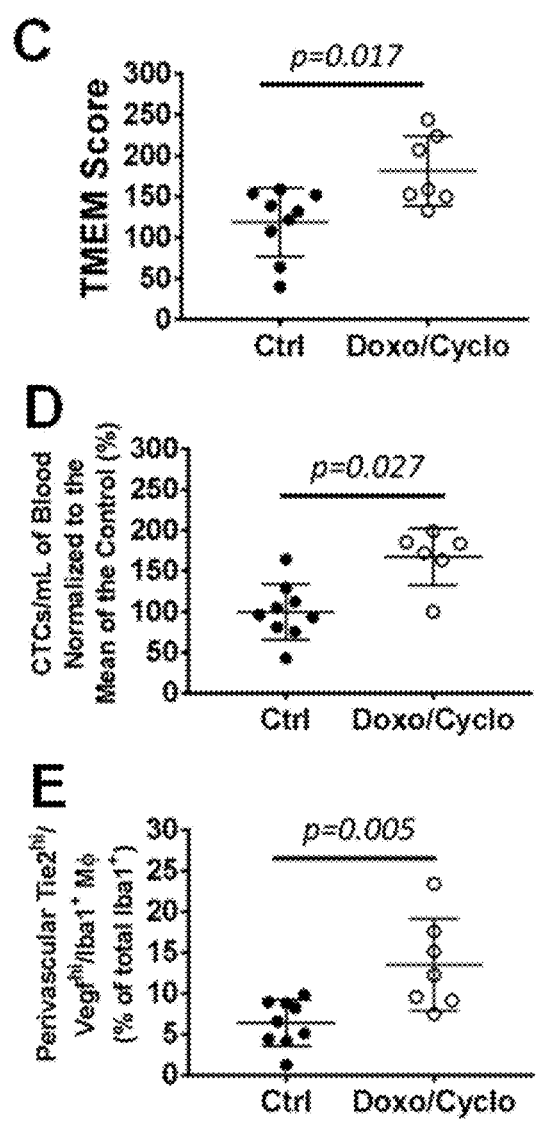

Doxorubicin/Cyclophosphamide Treatment Elicits Similar-to-Paclitaxel Pro-metastatic Changes in the Breast Cancer Microenvironment—Having shown that paclitaxel induces TMEM- and Mena-mediated pro-metastatic changes in the primary breast tumor microenvironment in a wide variety of mouse models, we then examined whether similar effects could be elicited by other chemotherapeutics. Doxorubicin/cyclophosphamide combinatorial chemotherapy was selected because it is a main component of neoadjuvant chemotherapy in human breast cancer patients (41, 42). Transgenic MMTV-PyMT mice bearing spontaneous breast tumors received a total of three doses of 5 mg/Kg doxorubicin i.v. every five days and 1 single dose of 120 mg/Kg cyclophosphamide i.p., as illustrated in FIG. 6A. Upon histological examination of the resulting tumors, necrosis and cell death were more evident in the doxorubicin/cyclophosphamide-treated tumors when compared to vehicle-treated mice (FIG. 6B). TMEM score was significantly (p<0.05) increased after doxorubicin/cyclophosphamide treatment (FIG. 6B-C), and was accompanied by a significant ~1.3-fold elevation in the number of circulating tumor cells (FIG. 6D), as well as increased numbers of perivascular Tie2$^{hi}$/Vegf$^{hi}$ macrophages compared to vehicle-treated controls (FIG. 6E). Therefore, doxorubicin/cyclophosphamide affects TMEM density, TMEM activity and CTCs in a similar fashion as paclitaxel treatment, further indicating that similar pro-metastatic effects may be elicited by a variety of neoadjuvant chemotherapy (NAC) regimes.

Figure 7A:
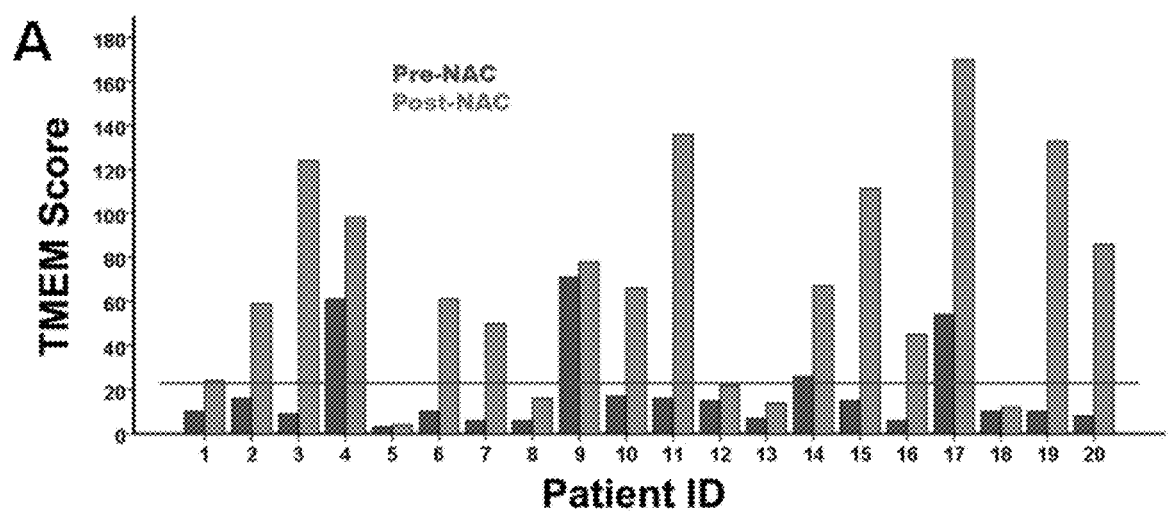
Figures 7B, 7C:
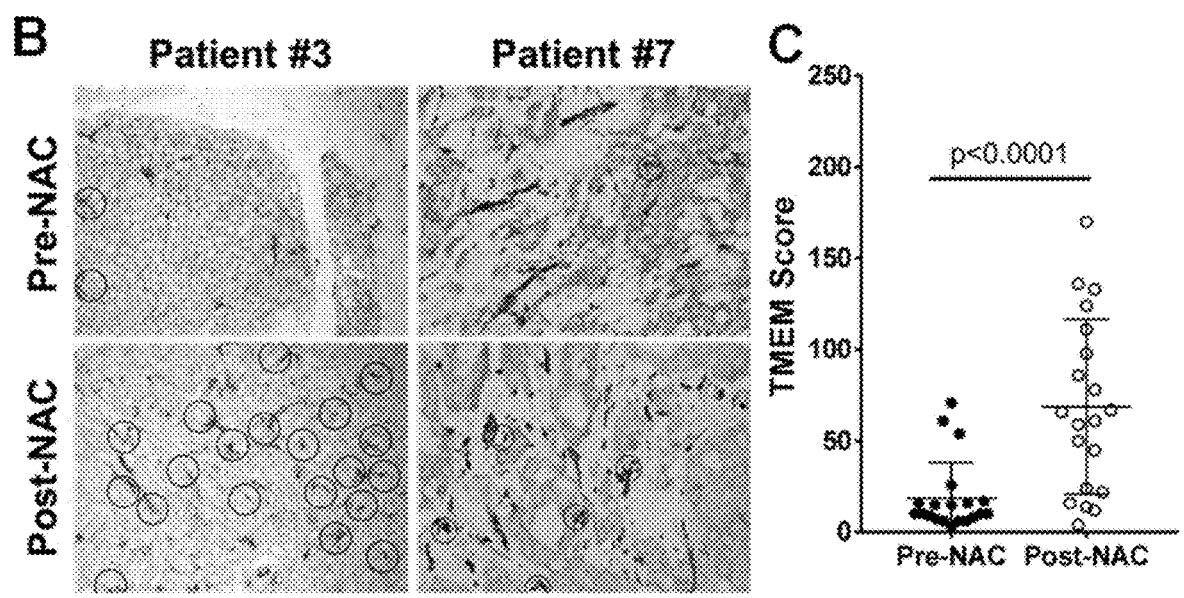

Neoadjuvant Chemotherapy with Paclitaxel Inclusion Induces Pro-metastatic Changes in the Tumor Microenvironment of Human Breast Cancer Patients—the investigations were expanded to human breast cancer patients. The change in TMEM density in post-NAC specimens was evaluated in 20 patients with ER$^+$/Her2$^-$ disease, treated with weekly paclitaxel for up to 12 weeks followed by 4 cycles of doxorubicin plus cyclophosphamide, and had residual disease after NAC (residual cancer burden [RCB] score 2-3). None of the patients received pre-operative Tamoxifen. When TMEM scores were graphed for each patient individually (FIG. 7A) the following observations were made: (I) an increase in TMEM score following NAC was observed in most patients, with a few representing notable fold-changes of >5 (e.g. patients #3, #11, #15, #19 and #20), (II) TMEM score from 50% of patients moved from low/intermediate into high-risk group (score of 23; red line in the graph) following NAC. TMEM score above 23 was established as the cutoff that separates patients into low/intermediate and high risk groups for developing distant metastasis (5), (III) in 15% of patients with already high TMEM score before the beginning of NAC, TMEM score remained unaltered or even worsened by the end of the treatment (e.g. patients #4, #9 and #17), (IV) there was not a single patient that demonstrated a decrease in TMEM score following NAC. Representative images of TMEM before and after NAC are shown for patients #3 and #7 (FIG. 7B). When analyzed as a cohort, the mean TMEM score was significantly increased (Wilcoxon test; p<0.0001) in post-NAC samples compared to pre-NAC core biopsies (FIG. 7C). These data suggest that NAC may have unwanted long term consequences in a certain subgroup of breast cancer patients.

Figures 7D, 7E, 7F:
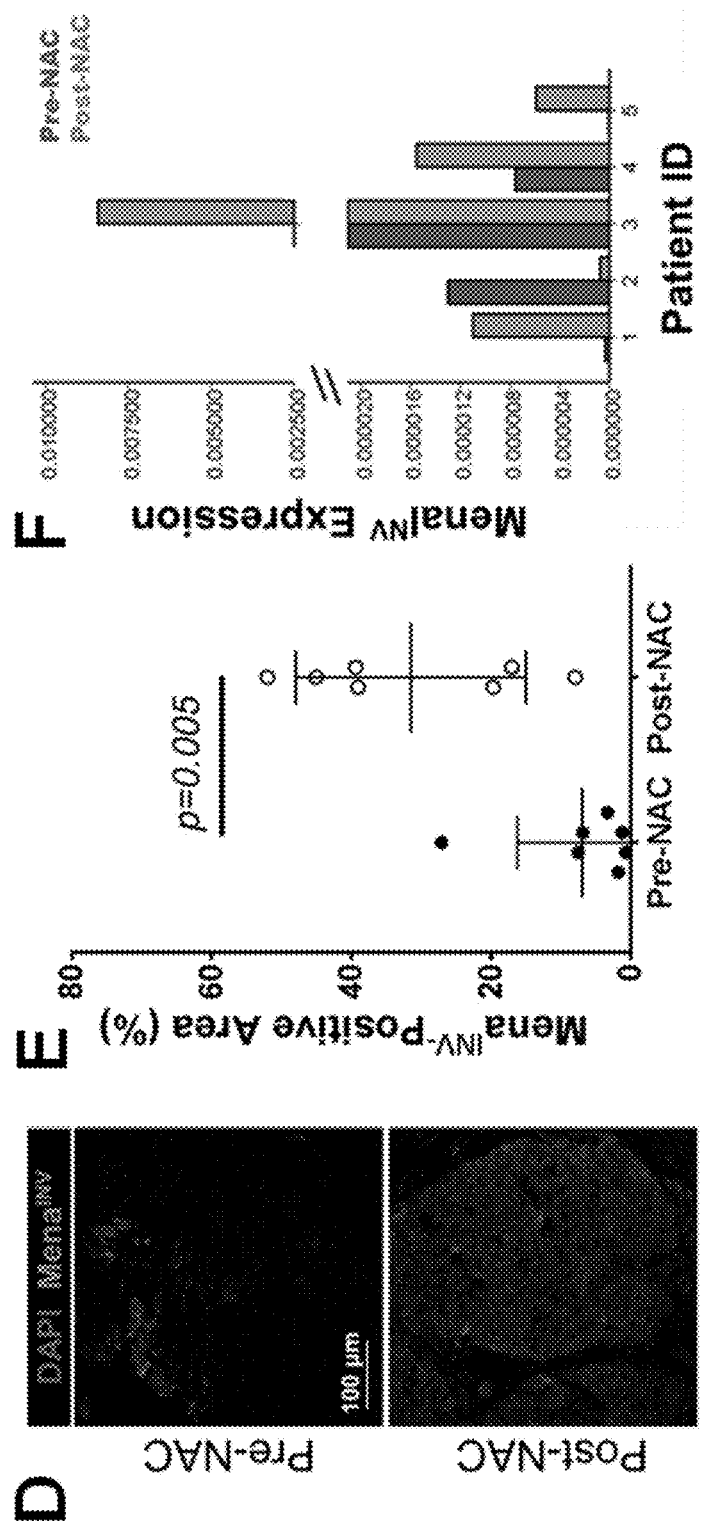

To further substantiate the translational importance of our preclinical data from PyMT and PDX mice receiving neoadjuvant paclitaxel into human breast cancer patients, we compared Mena$^{INV}$ expression levels in Pre- and Post-NAC samples. We observed a significant increase (p<0.01) in Mena$^{INV}$-positive area between pre-NAC biopsies and post-NAC tumors (FIGS. 7D-E). Additionally, we analyzed Mena$^{INV}$ expression by qRT-PCR in fine needle aspiration (FNA) biopsies taken before and one week after the second dose of weekly paclitaxel in an independent small cohort of patients (n=5). Even at such an early phase of paclitaxel treatment, we were able to observe an increase of Mena$^{INV}$ gene-expression in 4/5 breast cancer patients (Patients #1 and #3-5) (FIG. 7F), suggesting that the TMEM- and Mena-dependent pro-metastatic changes may have already been initiated in these patients.

Inhibition of the Tie2 Receptor Reverses the Paclitaxel-Mediated Pro-metastatic Changes—It was postulated that selective Tie2 inhibitors could not only be successfully used to counteract the angiogenic potential of NAC-induced endothelial progenitor cell infiltration as previously documented (9, 12, 13, 35, 36), but also the TMEM- and Mena-dependent pro-metastatic changes described in the current work, given that Tie2 inhibitors could additionally target TMEM-associated Tie2$^{hi}$/Vefg$^{hi}$ macrophages.

Figure 8A:
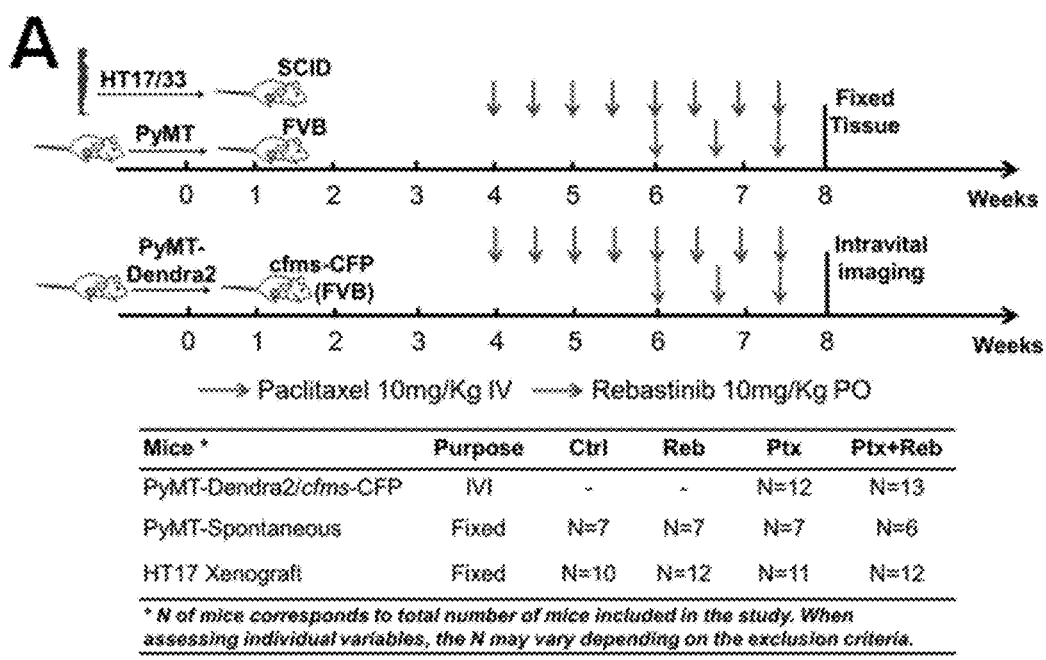
Figures 8B, 8C, 8D, 8E, 8F, 8G:
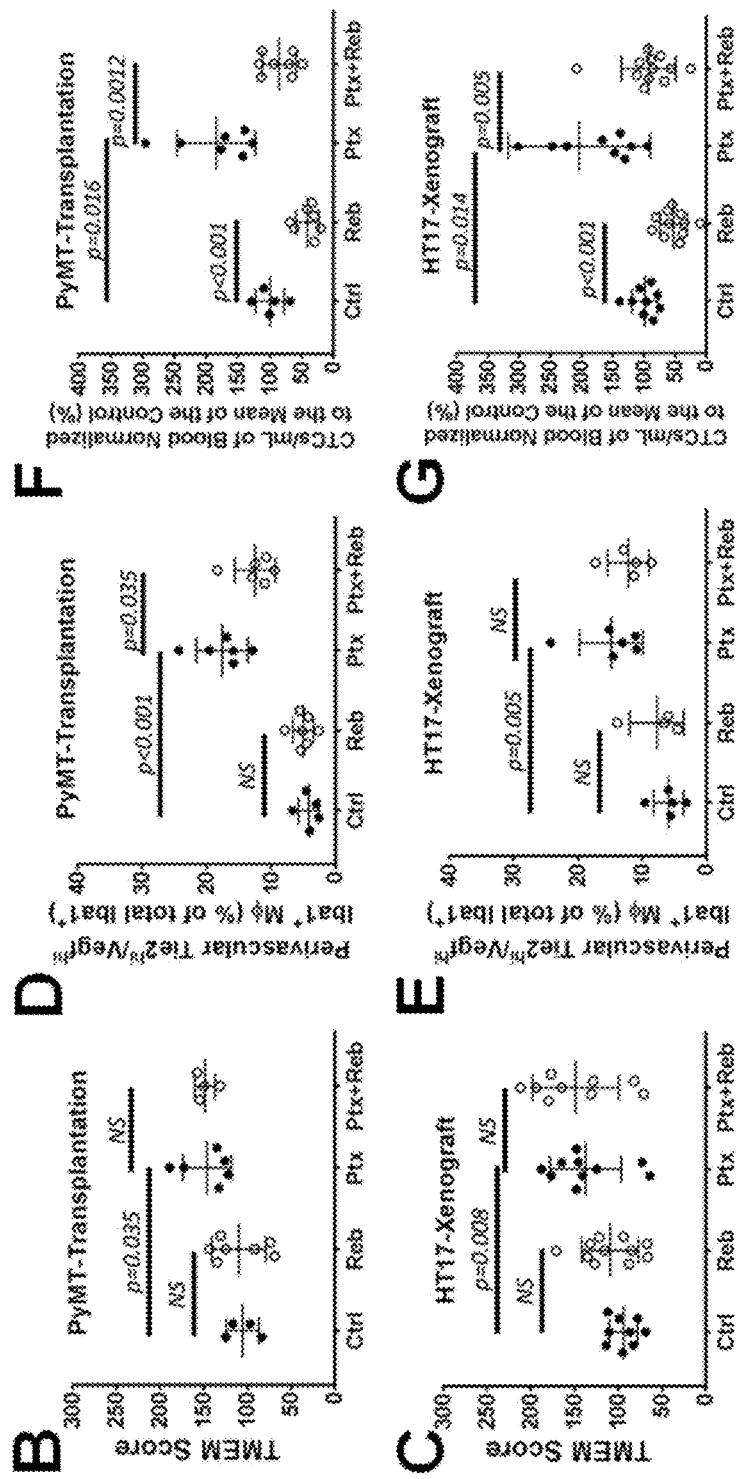

To address this question, the effects of rebastinib, a selective Tie2-inhibitor, were first investigated on TMEM assembly, vascular permeability and circulating tumor cells in the PyMT-transplantation and HT17 patient-derived xenograft mammary tumor cohorts used in our studies. Animals received chemotherapy with or without rebastinib as shown in FIG. 8A. Treatment with rebastinib alone did not significantly affect the overall TMEM score (FIG. 8B-C), or the density of perivascular Tie2$^{hi}$/Vegf$^{hi}$ macrophages (FIGS. 8D-E). However, it significantly (p<0.01) reduced the number of CTCs in both animal models (FIGS. 8F-G), thus significantly impairing hematogenous dissemination, without affecting the assembly of TMEM intravasation sites, indicating inhibition of TMEM activity.

Treatment with paclitaxel-only led to a significant increases in perivascular Tie2$^{hi}$/Vegf$^{hi}$ macrophages, TMEM assembly and activity as has been observed in all our earlier experiments (compare: FIG. 8B/C with 1B; FIG. 8D/E with 1D; FIG. 8F/G with 3F). More importantly, administration of rebastinib in paclitaxel-treated animals decreased the number of perivascular Tie2$^{hi}$/Vegf$^{hi}$ macrophages (FIG. 8D) and decreased circulating tumor cells to the level observed in the control animals (FIGS. 8F-G) without affecting TMEM assembly (FIGS. 8B-C). These data strongly indicate that Tie2 inhibition successfully blocks the function, but not the assembly of TMEM sites, which is sufficient to suppress cancer cell dissemination.

Next investigated was whether rebastinib-mediated suppression of tumor cell dissemination observed in the paclitaxel-treated mice was indeed due to inhibition of TMEM-associated macrophage function. To address this issue, IVI was used (FIG. 8A), and again found that baseline incidence and frequency of bursting, an activity uniquely associated with TMEM activity, were identical to the previously acquired data in the "paclitaxel-only" group (compare: FIGS. 8H-I with 3B-C). However, the co-administration of rebastinib in paclitaxel-treated mice completely abolished the incidence and frequency of bursting (FIG. 8H-I), suggesting that Tie2 inhibition blocks chemotherapy-driven TMEM-mediated vascular permeability and cancer cell dissemination.

Discussion

Accumulating evidence indicates that chemotherapy evokes a host-repair response, during which bone marrow-derived cells (BMDCs) infiltrate the primary tumor microenvironment and facilitate neo-angiogenesis and tumor regrowth (10, 11). Herein it is shown that through such BMDC recruitment, NAC may increase cancer cell dissemination and induce a more aggressive tumor phenotype leading to increased metastasis. The exact mechanism involves both the assembly of TMEM sites and the increased Mena$^{INV}$ expression in residual cancer after NAC. These results are consistent with our previous findings that Mena expression is required for TMEM assembly and for cancer cell dissemination through a TMEM, Mena$^{INV}$ and Tie2$^{hi}$/Vegf$^{hi}$-macrophage-dependent mechanism (1, 19, 20, 29). It should be noted that although the effects of taxanes and other chemotherapeutics on neovascularization have been adequately described (8, 10, 12, 13, 35, 44), our study provides insight on the mechanisms by which paclitaxel and other chemotherapy modulates the cancer microenvironment to promote breast cancer cell intravasation, and cancer cell dissemination to distant sites, as well as a Tie2-directed therapeutic approach to counteract paclitaxel-mediated induction of cancer cell dissemination (FIG. 8J). Thus, this work is primarily focused on the chemotherapy effect on cancer cell dissemination via TMEM/Mena-mediated mechanism, not on the development of clinically detectable metastases which involves other processes such as release from dormancy and tumor growth in addition to cancer cell dissemination.

It was demonstrated that chemotherapy increases macrophage density in PDX model, but not in spontaneous PyMT. Our findings in PyMT model are in discrepancy with Coussens group (45). This may be because of the use of 8-9-week old mice bearing early-stage spontaneous carcinomas, while the Coussens group worked with 12-week old mice which typically have advanced-stage tumors. However, our findings demonstrated that chemotherapy promotes an increase in perivascular Tie2$^{hi}$/Vegf$^{hi}$ macrophages (FIG. 8J), which is consistent with studies showing that this population associates with sites of (patho)physiological angiogenesis, especially as a host-repair mechanism following cytotoxic damage through chemotherapy (14, 15, 46-48). Although it is not clear if Tie2$^{hi}$/Vegf$^{hi}$ macrophages belong to the "classically activated" (M1) or "alternatively activated" (M2), they are crucial for modulating tumor microenvironment in response to cytotoxic therapies (10, 49). Our observation that other chemotherapeutics, i.e. doxorubicin/cyclophosphamide, are capable of perivascular Tie2$^{hi}$/Vegf$^{hi}$ macrophage recruitment, TMEM-assembly and TMEM-dependent tumor cell intravasation as well further supports the idea that the mechanism via which chemotherapy induces these pro-metastatic effects is a generic host-repair mechanism in response to extensive tissue damage and not a paclitaxel-specific phenomenon. For instance, it has been previously shown that Tie2$^{+}$ macrophages also express the chemokine receptor CXCR4, and that chemotherapy may increase the expression of the CXCR4 ligand CXCL12 in the primary tumor microenvironment (10). Therefore, it is very likely that the pro-metastatic Tie2$^{hi}$/Vegf$^{hi}$ macrophages are recruited through a distinct chemotactic axis in chemotherapy-treated individuals.

In addition, increased macrophage infiltration into tumors upon paclitaxel treatment increases the contact between tumor cells and macrophages, which is known to stimulate the expression of Mena$^{INV}$ via Notch pathway activation resulting in increased Mena$^{INV}$ and TMEM-dependent intravasation (27). These observations suggest that paclitaxel treatment may have induced Mena$^{INV}$ and Mena$^{Calc}$ expression due to chemotherapy-driven macrophage infiltration, leading to increased TMEM assembly and function as described here (FIG. 8J), and which may be an active process and not simply the result of selective survival of Mena-expressing tumor cells during paclitaxel treatment (50). Otherwise, our data are in agreement with findings from Oudin et al. (2016), who showed significantly increased Mena and Mena$^{INV}$ expression in paclitaxel-treated compared to control MDA-MB-213 xenografts (50).

The observed increase in disseminating tumor cells upon chemotherapy treatment as a direct consequence of macrophage contact-induced Mena$^{INV}$ overexpression is supported by two key findings reported here. First, Mena$^{INV}$ and Mena$^{Calc}$ expression correlated especially well with Tie2$^{hi}$ macrophages, consistent with prior studies in humans and in mice (18, 19, 29). Second, the absence of all Mena isoforms completely abolished cancer cell dissemination and distant metastasis in vivo, regardless of whether those mice received paclitaxel or not, and without affecting Tie2$^{hi}$/Vegf$^{hi}$ macrophage recruitment, indicating that Mena expression is an essential prerequisite for paclitaxel-induced breast cancer cell transendothelial migration in vivo.

The study indicates that the TMEM score and Mena$^{INV}$ increase in breast cancer samples from patients treated with NAC including doxorubicin, cyclophosphamide and paclitaxel, indicating that TMEM score and Mena$^{INV}$ might be used in predicting development of pro-metastatic changes in primary tumor microenvironment in response to NAC. This is significant given that many breast cancer patients are being treated with NAC which typically lasts about 6 months, and currently there are no markers that predict response to NAC (44). Our data indicate that in patients who have significant residual cancer burden (RCB) post-NAC, such as those with ER$^{+}$ disease, NAC might be inducing metastases via TMEM, in spite of inducing partial tumor regression. In particular, only 16.5% of patients with ER+/Her2− disease achieve pathologic complete response, indicating that our findings may apply to most patients with ER$^{+}$ disease treated with NAC (51). Interestingly, although addition of paclitaxel to NAC increases the percentage of patients with pathologic response (pCR) it does not improve the overall survival (6, 7) suggesting that some patients do not draw long term benefit from NAC. Since we showed that after only 2 doses of chemotherapy Mena$^{INV}$ increases in certain patients, we speculate that Mena isoform expression status in FNA biopsy after the first 2 weeks of chemotherapy could predict which patients would receive full benefit from NAC and in which continuation of NAC would be harmful. For example, an approach could be developed to routinely assess the levels of Mena$^{INV}$ in FNA samples after the $2^{nd}$ chemotherapeutic dose. If the levels of invasive isoforms of Mena do not increase, the chemotherapy could be continued to its completion. However, if there is an increase in the invasive Mena isoform levels the chemotherapy could be discontinued and these patients could be treated with surgery first followed by chemotherapy.

Our cohort of 20 patients with ER$^{+}$ disease had only 5 year follow up time which is not sufficient to reliably analyze distant recurrence in this breast cancer subtype because ER$^{+}$ disease often recurs 10 or more years after the initial diagnosis (52). However, three retrospective-prospective analyses of human breast cancer samples indicate that increased TMEM score is associated with metastatic outcome in patients (3, 5, 53). These studies imply that with the proper follow up time the increase in TMEM score upon chemotherapy will translate in distant recurrence in some of the patients. A follow up study is needed to determine with certainty if patients with increase in TMEM score upon NAC indeed develop distant recurrence more often than those without increase in TMEM score. In addition, as discussed above, it is necessary to determine if we can predict which patients are likely to respond to NAC with increase in Mena$^{INV}$ so that the treatment can be adjusted accordingly.

To accurately reflect clinically relevant scenarios we primarily used early-stage PyMT tumors in our study. As reported by American Cancer Society in "Breast cancer facts and figures 2015-2106" the incidence rate is the highest for tumors <2 cm (70 per 100,000), followed by tumors 2-4.9 cm (35 per 100,000) (32). Tumors >5 cm had the incidence rate of only 10 per 100,000. Likewise, incidence rate for localized (40-90) and regional (25-40) disease far exceeds the incidence rate for distant (5-11) disease (32). In addition, by selecting early-stage PyMT tumors, measuring potentially TMEM-independent mechanisms of cancer cell dissemination that could result from an open-circulation effect have been avoided, i.e. upon destruction of the blood vasculature in advanced stage necrotic lesions.

Our findings that paclitaxel induces increase in CTCs (FIG. 3F) is consistent with recently reported data from patient studies focused on the effect of chemotherapy on CTCs. Although CTC count measured by FDA-approved CellSearch System is a strong prognostic factor in both primary and metastatic breast cancer there is no conclusive evidence in the literature that chemotherapy significantly reduces CTCs (54). On the contrary, several reports indicate that CTC counts in post-chemotherapy blood samples increase in some patients and decrease others, do not correlate with pathologic complete response and correlate with the distant-metastasis-free survival (55, 56). Moreover, when CTC search included cells with epithelial-mesenchymal transition marker expression, 21% of patients showed increased CTC counts post NAC, while 15% showed decrease in CTCs counts post NAC (56). Thus our data indicating that NAC may be increasing CTCs in some patients are consistent with current literature.

Since metastatic disease is the major cause of cancer-related mortality and currently incurable, it is critical that we develop strategies to prevent progression of cancer to metastatic stage and to prevent further spread from already existing metastatic foci. Therefore, our finding that chemotherapy, when given in the setting of clinically active disease, promotes cancer cell dissemination is of major concern. However, our data indicate that strategies can be developed to prevent chemotherapy induced TMEM/Mena-mediated cancer cell dissemination and subsequent metastasis. This can be done either by discontinuing NAC in patients whose tumors show NAC-induced pro-metastatic changes, or by combining NAC with agents that block TMEM/Mena-mediated cancer cell dissemination, such as selective Tie2 inhibitors (FIG. 8J), which would be useful not only in NAC treatment of localized breast cancer, but also in treatment of metastatic breast cancer.

Materials and Methods

Drug Administration. The following drugs were administered in mice: Paclitaxel was given at 10 mg/Kg i.v every 5 days for 2 weeks; Doxorubicin was given at 5 mg/Kg i.v. every 5 days for 2 weeks; Cyclophosphamide was given at 120 mg/Kg i.p. only once; Rebastinib was given at 10 mg/Kg per os, every 3-4 days for 4 weeks.

Animals and Animal Procedures. MMTV-PyMT mice were bred in-house at the Albert Einstein College of Medicine (AECOM). Generation of MMTV-PyMT Mena$^{-/-}$ has been described previously (28). CFP- or Dendra2-labeled mammary carcinoma cells were generated on the FVB background by co-injection of Tg(MMTV-iCRE)1jwp together with Tg(PCAG-loxp-CATstop-loxp-CFP) or Tg(loxP-stop-loxP-PDendra2)jwp plasmids, respectively, by conventional methods in the Albert Einstein Transgenic Mouse Facility. All syngeneic transplantation models were generated through orthotopic transplantation of 1 mm×1 mm tumor chunks, using tumors of 1 cm-diameter from 12-16-week old MMTV-PyMT mena−/− or mena+/+ donor mice into 5-6 week-old FVB recipients. Tumor chunks were implanted on the fourth mammary pad on the left side. The generation of the ER$^-$ HT17 and ER$^+$ HT33 patient-derived xenografts has been described previously (31). Animal handling and associated procedures were approved by the Institutional Animal Care and Use Committee (IACUC). Additional information is detailed in Supplementary Methods.

Intravital Imaging. Intravital imaging was performed using a custom-built two-laser multiphoton microscope, as previously described (57). Mice were anesthetized using 0.75-2.5% isofluorane, depilated. A skin flap procedure, previously developed (58), was performed by exposing the 4$^{th}$ or 5$^{th}$ mammary fat pad. Given the early stage of carcinoma and small tumor size, this necessitated the development of a custom fixturing technique where the exposed tissue was stabilized by affixing the edge of a 10-mm window fitted with an 8-mm clear aperture respectively with cyanoacrylate. The mouse was then placed on a fixturing plate, fitted to the respective window, on the microscope xy stage and imaging was performed in the center of the window away from the glue. The animal was placed in a heated chamber, AirTherm ATX forced air heater (WPI Inc.), maintained at physiologic temperature during the course of imaging, and supplemented with 50-100 uL of PBS per hour via the tail vein catheter. As previously described (1), three milligrams of 155-kDa TMR-dextran (Sigma) were administered via the catheter to visualize the vasculature. All images were reconstructed and analyzed in ImageJ (59), as described in Supplementary Methods.

Histology and TMEM Immunohistochemistry. Breast tumors and lungs were isolated, rinsed in PBS, fixed in 10% neutral buffered formalin for 48 hours, dehydrated and embedded in paraffin. Sections (5 μm) were stained with H & E or TMEM triple-stain immunohistochemistry, as previously described (3).

Immunofluorescence. Slides were deparaffinized by melting at 60° C. in an oven equipped with a fan for 20 minutes, followed by 2× xylene treatment for 20 minutes. Slides were rehydrated and antigen retrieval was done in 1 mM EDTA (pH 8.0) or 1× citrate buffer (pH 6.0) (Diagnostic BioSystems) at 97° C. for 20 minutes in a conventional steamer. Endogenous peroxidase was blocked by using 0.3% hydrogen peroxide in water, followed by incubation of slides in a blocking buffer solution (10% FBS, 1% BSA, 0.0025% fish skin gelatin in 0.05% PBST) for 60 minutes at room temperature. The following primary antibodies were used in different combinations, depending on the experiment: chicken anti-Mena$^{INV}$ (0.25 ug/mL, generated in-house in the lab of John S. Condeelis), rabbit anti-Cd31 (1:400;

77699s; Cell Signaling), rabbit anti-Vegf (1:2,000; Rb 9031-PO-A; Thermo), rat anti-Tie2 (1:100; 16-5987-82; eBioscience), rabbit anti-Iba1 (1:6,000; 019-19741; Wako), rat anti-endomucin (1:500; sc-65495; Santa Cruz), rabbit anti-TMR (1:1,000; A-6397; Life Technologies). Secondary antibody treatment was performed using HRP-conjugated antibodies, and was followed by tyramide signal amplification (TSA), using the Perkin Elmer; Opal™ 4-color Fluorescent IHC kit, according to the manufacturer's directions. All slides were imaged on the Pannoramic 250 Flash II digital whole slide scanner, using a 20×0.75NA objective lens. Image analysis was performed in ImageJ, detailed in Supplementary Methods.

Gene Expression Analysis. Total RNA was extracted from formalin-fixed paraffin-embedded (FFPE) tissues using deparaffinization solution (Qiagen) and RNeasy FFPE Kit (Qiagen), followed by DNase treatment. An RT-PCR method SYBR Green (Qiagen) was used to measure expression levels of total Mena (PanMena), as well as of the specific Mena isoforms, Mena11a and Mena$^{INV}$, as described (29), with slight modifications, as detailed in Supplementary Methods. Mena$^{Calc}$ expression has been previously defined as the expression level of all Mena isoforms combined after subtraction of Mena 11a from PanMena (2).

Circulating Tumor Cells. Mice were anesthetized with 3.5-4.5% isoflurane, and blood was taken from the right ventricle by heart puncture, using 25G needles coated with heparin. Erythrocytes were lysed, using 10 ml of 1×RBC lysis buffer (multi-species, eBioscience). Cancer cells were quantified, as previously described (31, 60).

Statistical analysis. All statistical tests are justified for every figure. Sample size was calculated based on significance level (adjusted for sidedness) of 0.025, probability of type II error of 0.2 (statistical power of 0.8) and expected difference in means equal to 1.2 standard deviation (SD) units, based on the assumption that the SD of the response variable was 1 unit. Data are presented as dot plots with their means and SDs. Significant differences between groups were determined using nonparametric statistical tests, i.e. the Mann-Whitney U-test for unpaired and Wilcoxon test for paired samples. Correlations were performed using Pearson's correlation and coefficient of determination ($R^2$), and data are presented as scatterplots with fit-lines and p-values. To investigate for differences of a binary outcome (i.e. incidence of metastasis) between two groups, cross-tabulation and chi-square tests were performed. All p-values of <0.1 are reported in graphs, but significance level for statistical testing was set to p<0.05.

REFERENCES

1. A. S. Harney, E. N. Arwert, D. Entenberg, Y. Wang, P. Guo, B. Z. Qian, M. H. Oktay, J. W. Pollard, J. G. Jones, J. S. Condeelis, Real-Time Imaging Reveals Local, Transient Vascular Permeability, and Tumor Cell Intravasation Stimulated by TIE2hi Macrophage-Derived VEGFA. *Cancer Discov* 5, 932-943 (2015); published online EpubSep (10.1158/2159-8290.CD-15-0012).
2. G. S. Karagiannis, S. Goswami, J. G. Jones, M. H. Oktay, J. S. Condeelis, Signatures of breast cancer metastasis at a glance. *J Cell Sci* 129, 1751-1758 (2016); published online EpubMay 1 (10.1242/jcs.183129).
3. B. D. Robinson, G. L. Sica, Y. F. Liu, T. E. Rohan, F. B. Gertler, J. S. Condeelis, J. G. Jones, Tumor microenvironment of metastasis in human breast carcinoma: a potential prognostic marker linked to hematogenous dissemination. *Clin Cancer Res* 15, 2433-2441 (2009); published online EpubApr 1 (10.1158/1078-0432.CCR-08-2179).
4. M. H. Oktay, F. B. Gertler, Y. F. Liu, T. E. Rohan, J. S. Condeelis, J. G. Jones, Correlated immunohistochemical and cytological assays for the prediction of hematogenous dissemination of breast cancer. *J. Histochem. Cytochem.* 60, 168-173 (2012); published online EpubMar (10.1369/0022155411435153).
5. T. E. Rohan, X. Xue, H. M. Lin, T. M. D'Alfonso, P. S. Ginter, M. H. Oktay, B. D. Robinson, M. Ginsberg, F. B. Gertler, A. G. Glass, J. A. Sparano, J. S. Condeelis, J. G. Jones, Tumor microenvironment of metastasis and risk of distant metastasis of breast cancer. *J Natl Cancer Inst* 106, (2014); published online EpubAug (10.1093/jnci/dju136).
6. P. Rastogi, S. J. Anderson, H. D. Bear, C. E. Geyer, M. S. Kahlenberg, A. Robidoux, R. G. Margolese, J. L. Hoehn, V. G. Vogel, S. R. Dakhil, D. Tamkus, K. M. King, E. R. Pajon, M. J. Wright, J. Robert, S. Paik, E. P. Mamounas, N. Wolmark, Preoperative chemotherapy: updates of National Surgical Adjuvant Breast and Bowel Project Protocols B-18 and B-27. *J Clin Oncol* 26, 778-785 (2008); published online EpubFeb 10 (10.1200/JCO.2007.15.0235).
7. L. Gianni, J. Baselga, W. Eiermann, V. G. Porta, V. Semiglazov, A. Lluch, M. Zambetti, D. Sabadell, G. Raab, A. L. Cussac, A. Bozhok, A. Martinez-Agullo, M. Greco, M. Byakhov, J. J. Lopez, M. Mansutti, P. Valagussa, G. Bonadonna, Phase III trial evaluating the addition of paclitaxel to doxorubicin followed by cyclophosphamide, methotrexate, and fluorouracil, as adjuvant or primary systemic therapy: European Cooperative Trial in Operable Breast Cancer. *Journal of clinical oncology: official journal of the American Society of Clinical Oncology* 27, 2474-2481 (2009); published online EpubMay 20 (10.1200/JCO.2008.19.2567).
8. L. G. Daenen, J. M. Houthuijzen, G. A. Cirkel, J. M. Roodhart, Y. Shaked, E. E. Voest, Treatment-induced host-mediated mechanisms reducing the efficacy of antitumor therapies. *Oncogene* 33, 1341-1347 (2014); published online EpubMar 13 (10.1038/onc.2013.94).
9. M. De Palma, C. E. Lewis, Macrophage regulation of tumor responses to anticancer therapies. *Cancer Cell* 23, 277-286 (2013); published online EpubMar 18 (10.1016/j.ccr.2013.02.013).
10. R. Hughes, B. Z. Qian, C. Rowan, M. Muthana, I. Keklikoglou, O. C. Olson, S. Tazzyman, S. Danson, C. Addison, M. Clemons, A. M. Gonzalez-Angulo, J. A. Joyce, M. De Palma, J. W. Pollard, C. E. Lewis, Perivascular M2 Macrophages Stimulate Tumor Relapse after Chemotherapy. *Cancer Res* 75, 3479-3491 (2015); published online EpubSep 01 (10.1158/0008-5472.CAN-14-3587).
11. J. M. Roodhart, H. He, L. G. Daenen, A. Monvoisin, C. L. Barber, M. van Amersfoort, J. J. Hofmann, F. Radtke, T. F. Lane, E. E. Voest, M. L. Iruela-Arispe, Notch1 regulates angio-supportive bone marrow-derived cells in mice: relevance to chemoresistance. *Blood* 122, 143-153 (2013); published online EpubJul 4 (10.1182/blood-2012-11-459347).
12. Y. Shaked, A. Ciarrocchi, M. Franco, C. R. Lee, S. Man, A. M. Cheung, D. J. Hicklin, D. Chaplin, F. S. Foster, R. Benezra, R. S. Kerbel, Therapy-induced acute recruitment of circulating endothelial progenitor cells to tumors. *Science* 313, 1785-1787 (2006); published online EpubSep 22 (10.1126/science.1127592).

13. Y. Shaked, E. Henke, J. M. Roodhart, P. Mancuso, M. H. Langenberg, M. Colleoni, L. G. Daenen, S. Man, P. Xu, U. Emmenegger, T. Tang, Z. Zhu, L. Witte, R. M. Strieter, F. Bertolini, E. E. Voest, R. Benezra, R. S. Kerbel, Rapid chemotherapy-induced acute endothelial progenitor cell mobilization: implications for antiangiogenic drugs as chemosensitizing agents. *Cancer Cell* 14, 263-273 (2008); published online EpubSep 09 (10.1016/j.ccr.2008.08.001).

14. M. De Palma, M. A. Venneri, R. Galli, L. Sergi Sergi, L. S. Politi, M. Sampaolesi, L. Naldini, Tie2 identifies a hematopoietic lineage of proangiogenic monocytes required for tumor vessel formation and a mesenchymal population of pericyte progenitors. *Cancer Cell* 8, 211-226 (2005); published online EpubSep (10.1016/j.ccr.2005.08.002).

15. M. De Palma, M. A. Venneri, C. Roca, L. Naldini, Targeting exogenous genes to tumor angiogenesis by transplantation of genetically modified hematopoietic stem cells. *Nat Med* 9, 789-795 (2003); published online EpubJun (10.1038/nm871).

16. A. Dovas, A. Patsialou, A. S. Harney, J. Condeelis, D. Cox, Imaging interactions between macrophages and tumour cells that are involved in metastasis in vivo and in vitro. *J Microsc* 251, 261-269 (2013); published online EpubSep (10.1111/j.1365-2818.2012.03667.x).

17. A. Patsialou, J. J. Bravo-Cordero, Y. Wang, D. Entenberg, H. Liu, M. Clarke, J. S. Condeelis, Intravital multiphoton imaging reveals multicellular streaming as a crucial component of in vivo cell migration in human breast tumors. *Intravital* 2, e25294 (2013); published online EpubApr 1 (10.4161/intv.25294).

18. E. T. Roussos, J. S. Condeelis, A. Patsialou, Chemotaxis in cancer. *Nat Rev Cancer* 11, 573-587 (2011); published online EpubAug (10.1038/nrc3078).

19. E. T. Roussos, S. Goswami, M. Balsamo, Y. Wang, R. Stobezki, E. Adler, B. D. Robinson, J. G. Jones, F. B. Gertler, J. S. Condeelis, M. H. Oktay, Mena invasive (Mena(INV)) and Mena11a isoforms play distinct roles in breast cancer cell cohesion and association with TMEM. *Clin Exp Metastasis* 28, 515-527 (2011); published online EpubAug (10.1007/s10585-011-9388-6).

20. E. T. Roussos, M. Balsamo, S. K. Alford, J. B. Wyckoff, B. Gligorijevic, Y. Wang, M. Pozzuto, R. Stobezki, S. Goswami, J. E. Segall, D. A. Lauffenburger, A. R. Bresnick, F. B. Gertler, J. S. Condeelis, Mena invasive (MenaINV) promotes multicellular streaming motility and transendothelial migration in a mouse model of breast cancer. *J Cell Sci* 124, 2120-2131 (2011); published online EpubJul 1 (10.1242/jcs.086231).

21. J. Wyckoff, W. Wang, E. Y. Lin, Y. Wang, F. Pixley, E. R. Stanley, T. Graf, J. W. Pollard, J. Segall, J. Condeelis, A paracrine loop between tumor cells and macrophages is required for tumor cell migration in mammary tumors. *Cancer Res* 64, 7022-7029 (2004); published online EpubOct 1 (10.1158/0008-5472.CAN-04-1449).

22. U. Philippar, E. T. Roussos, M. Oser, H. Yamaguchi, H. D. Kim, S. Giampieri, Y. Wang, S. Goswami, J. B. Wyckoff, D. A. Lauffenburger, E. Sahai, J. S. Condeelis, F. B. Gertler, A Mena invasion isoform potentiates EGF-induced carcinoma cell invasion and metastasis. *Dev Cell* 15, 813-828 (2008); published online EpubDec (10.1016/j.devcel.2008.09.003).

23. A. Patsialou, J. Wyckoff, Y. Wang, S. Goswami, E. R. Stanley, J. S. Condeelis, Invasion of human breast cancer cells in vivo requires both paracrine and autocrine loops involving the colony-stimulating factor-1 receptor. *Cancer Res* 69, 9498-9506 (2009); published online EpubDec 15 (10.1158/0008-5472.CAN-09-1868).

24. S. Goswami, E. Sahai, J. B. Wyckoff, M. Cammer, D. Cox, F. J. Pixley, E. R. Stanley, J. E. Segall, J. S. Condeelis, Macrophages promote the invasion of breast carcinoma cells via a colony-stimulating factor-1/epidermal growth factor paracrine loop. *Cancer Res* 65, 5278-5283 (2005); published online EpubJun 15 (10.1158/0008-5472.CAN-04-1853).

25. E. Leung, A. Xue, Y. Wang, P. Rougerie, V. P. Sharma, R. Eddy, D. Cox, J. Condeelis, Blood vessel endothelium-directed tumor cell streaming in breast tumors requires the HGF/C-Met signaling pathway. *Oncogene*, (2016); published online EpubNov 28 (10.1038/onc.2016.421).

26. S. Goswami, U. Philippar, D. Sun, A. Patsialou, J. Avraham, W. Wang, F. Di Modugno, P. Nistico, F. B. Gertler, J. S. Condeelis, Identification of invasion specific splice variants of the cytoskeletal protein Mena present in mammary tumor cells during invasion in vivo. *Clin Exp Metastasis* 26, 153-159 (2009)10.1007/s10585-008-9225-8).

27. J. Pignatelli, J. J. Bravo-Cordero, M. Roh-Johnson, S. J. Gandhi, Y. Wang, X. Chen, R. J. Eddy, A. Xue, R. H. Singer, L. Hodgson, M. H. Oktay, J. S. Condeelis, Macrophage-dependent tumor cell transendothelial migration is mediated by Notch1/MenaINV-initiated invadopodium formation. *Sci Rep* 6, 37874 (2016); published online EpubNov 30 (10.1038/srep37874).

28. E. T. Roussos, Y. Wang, J. B. Wyckoff, R. S. Sellers, W. Wang, J. Li, J. W. Pollard, F. B. Gertler, J. S. Condeelis, Mena deficiency delays tumor progression and decreases metastasis in polyoma middle-T transgenic mouse mammary tumors. *Breast Cancer Res* 12, R101 (2010) 10.1186/bcr2784).

29. J. Pignatelli, S. Goswami, J. G. Jones, T. E. Rohan, E. Pieri, X. Chen, E. Adler, D. Cox, S. Maleki, A. Bresnick, F. B. Gertler, J. S. Condeelis, M. H. Oktay, Invasive breast carcinoma cells from patients exhibit MenaINV- and macrophage-dependent transendothelial migration. *Sci Signal* 7, ra112 (2014)10.1126/scisignal.2005329).

30. L. Chen, J. Li, F. Wang, C. Dai, F. Wu, X. Liu, T. Li, R. Glauben, Y. Zhang, G. Nie, Y. He, Z. Qin, Tie2 expression on macrophages is required for blood vessel reconstruction and tumor relapse after chemotherapy. *Cancer research*, (2016); published online EpubOct 10 (10.1158/0008-5472.CAN-16-1114).

31. A. Patsialou, Y. Wang, J. Lin, K. Whitney, S. Goswami, P. A. Kenny, J. S. Condeelis, Selective gene-expression profiling of migratory tumor cells in vivo predicts clinical outcome in breast cancer patients. *Breast Cancer Res* 14, R139 (2012); published online EpubOct 31 (10.1186/bcr3344).

32. A. C. Society, Breast Cancer Facts & Figures 2015-2016. Atlanta. *American Cancer Society, Inc.*, (2015).

33. T. Shree, O. C. Olson, B. T. Elie, J. C. Kester, A. L. Garfall, K. Simpson, K. M. Bell-McGuinn, E. C. Zabor, E. Brogi, J. A. Joyce, Macrophages and cathepsin proteases blunt chemotherapeutic response in breast cancer. *Genes & development* 25, 2465-2479 (2011); published online EpubDec 1 (10.1101/gad.180331.111).

34. F. Pucci, M. A. Venneri, D. Biziato, A. Nonis, D. Moi, A. Sica, C. Di Serio, L. Naldini, M. De Palma, A distinguishing gene signature shared by tumor-infiltrating Tie2-expressing monocytes, blood "resident" monocytes, and embryonic macrophages suggests common functions 35. C. Murdoch, M. Muthana, S. B. Coffelt, C. E. Lewis, The role of myeloid cells in the promotion of tumour angiogenesis. *Nature reviews. Cancer* 8, 618-631 (2008); published online EpubAug (10.1038/nrc2444).
36. C. E. Lewis, A. S. Harney, J. W. Pollard, The Multifaceted Role of Perivascular Macrophages in Tumors. *Cancer cell* 30, 18-25 (2016); published online EpubJul 11 (10.1016/j.ccell.2016.05.017).
37. E. Fremder, M. Munster, A. Aharon, V. Miller, S. Gingis-Velitski, T. Voloshin, D. Alishekevitz, R. Bril, S. J. Scherer, D. Loven, B. Brenner, Y. Shaked, Tumor-derived microparticles induce bone marrow-derived cell mobilization and tumor homing: a process regulated by osteopontin. *International journal of cancer. Journal international du cancer* 135, 270-281 (2014); published online EpubJul 15 (10.1002/ijc.28678).
38. C. L. Forse, S. Agarwal, D. Pinnaduwage, F. Gertler, J. S. Condeelis, J. Lin, X. Xue, K. Johung, A. M. Mulligan, T. E. Rohan, S. B. Bull, I. L. Andrulis, Mena(calc), a quantitative method of metastasis assessment, as a prognostic marker for axillary node-negative breast cancer. *BMC Cancer* 15, 483 (2015)10.1186/s12885-015-1468-6).
39. S. Agarwal, F. B. Gertler, M. Balsamo, J. S. Condeelis, R. L. Camp, X. Xue, J. Lin, T. E. Rohan, D. L. Rimm, Quantitative assessment of invasive mena isoforms (Menacalc) as an independent prognostic marker in breast cancer. *Breast Cancer Res* 14, R124 (2012); published online EpubSep 12 (10.1186/bcr3318).
40. M. J. Oudin, S. K. Hughes, N. Rohani, M. N. Moufarrej, J. G. Jones, J. S. Condeelis, D. A. Lauffenburger, F. B. Gertler, Characterization of the expression of the pro-metastatic Mena(INV) isoform during breast tumor progression. *Clinical & experimental metastasis* 33, 249-261 (2016); published online EpubMar (10.1007/s10585-015-9775-5).
41. G. Bonadonna, A. Moliterni, M. Zambetti, M. G. Daidone, S. Pilotti, L. Gianni, P. Valagussa, 30 years' follow up of randomised studies of adjuvant CMF in operable breast cancer: cohort study. *Bmj* 330, 217 (2005); published online EpubJan 29 (10.1136/bmj.38314.622095.8F).
42. G. Bonadonna, E. Brusamolino, P. Valagussa, A. Rossi, L. Brugnatelli, C. Brambilla, M. De Lena, G. Tancini, E. Bajetta, R. Musumeci, U. Veronesi, Combination chemotherapy as an adjuvant treatment in operable breast cancer. *The New England journal of medicine* 294, 405-410 (1976); published online EpubFeb 19 (10.1056/NEJM197602192940801).
44. J. M. Roodhart, M. H. Langenberg, J. S. Vermaat, M. P. Lolkema, A. Baars, R. R. Giles, E. O. Witteveen, E. E. Voest, Late release of circulating endothelial cells and endothelial progenitor cells after chemotherapy predicts response and survival in cancer patients. *Neoplasia* 12, 87-94 (2010); published online EpubJan
45. D. G. DeNardo, D. J. Brennan, E. Rexhepaj, B. Ruffell, S. L. Shiao, S. F. Madden, W. M. Gallagher, N. Wadhwani, S. D. Keil, S. A. Junaid, H. S. Rugo, E. S. Hwang, K. Jirstrom, B. L. West, L. M. Coussens, Leukocyte complexity predicts breast cancer survival and functionally regulates response to chemotherapy. *Cancer Discov* 1, 54-67 (2011); published online EpubJun (10.1158/2159-8274.CD-10-0028).
46. C. Murdoch, S. Tazzyman, S. Webster, C. E. Lewis, Expression of Tie-2 by human monocytes and their responses to angiopoietin-2. *Journal of immunology* 178, 7405-7411 (2007).
47. M. A. Venneri, M. De Palma, M. Ponzoni, F. Pucci, C. Scielzo, E. Zonari, R. Mazzieri, C. Doglioni, L. Naldini, Identification of proangiogenic TIE2-expressing monocytes (TEMs) in human peripheral blood and cancer. *Blood* 109, 5276-5285 (2007); published online EpubJun 15 (10.1182/blood-2006-10-053504).
48. M. De Palma, L. Naldini, Angiopoietin-2 TIEs up macrophages in tumor angiogenesis. *Clinical cancer research: an official journal of the American Association for Cancer Research* 17, 5226-5232 (2011); published online EpubAug 15 (10.1158/1078-0432.CCR-10-0171).
49. C. E. Lewis, A. S. Harney, J. W. Pollard, The Multifaceted Role of Perivascular Macrophages in Tumors. *Cancer Cell* 30, 365 (2016); published online EpubAug 08 (10.1016/j.ccell.2016.07.009).
50. M. J. Oudin, L. Barbier, C. Schafer, T. Kosciuk, M. A. Miller, S. Han, O. Jonas, D. A. Lauffenburger, F. B. Gertler, MENA Confers Resistance to Paclitaxel in Triple-Negative Breast Cancer. *Mol Cancer Ther* 16, 143-155 (2017); published online EpubJan (10.1158/1535-7163.MCT-16-0413).
51. S. K. Swisher, J. Vila, S. L. Tucker, I. Bedrosian, S. F. Shaitelman, J. K. Litton, B. D. Smith, A. S. Caudle, H. M. Kuerer, E. A. Mittendorf, Locoregional Control According to Breast Cancer Subtype and Response to Neoadjuvant Chemotherapy in Breast Cancer Patients Undergoing Breast-conserving Therapy. *Ann Surg Oncol* 23, 749-756 (2016); published online EpubMar (10.1245/s10434-015-4921-5).
52. F. M. Blows, K. E. Driver, M. K. Schmidt, A. Broeks, F. E. van Leeuwen, J. Wesseling, M. C. Cheang, K. Gelmon, T. O. Nielsen, C. Blomqvist, P. Heikkila, T. Heikkinen, H. Nevanlinna, L. A. Akslen, L. R. Begin, W. D. Foulkes, F. J. Couch, X. Wang, V. Cafourek, J. E. Olson, L. Baglietto, G. G. Giles, G. Severi, C. A. McLean, M. C. Southey, E. Rakha, A. R. Green, I. O. Ellis, M. E. Sherman, J. Lissowska, W. F. Anderson, A. Cox, S. S. Cross, M. W. Reed, E. Provenzano, S. J. Dawson, A. M. Dunning, M. Humphreys, D. F. Easton, M. Garcia-Closas, C. Caldas, P. D. Pharoah, D. Huntsman, Subtyping of breast cancer by immunohistochemistry to investigate a relationship between subtype and short and long term survival: a collaborative analysis of data for 10,159 cases from 12 studies. *PLoS Med* 7, e1000279 (2010); published online EpubMay 25 (10.1371/journal.pmed.1000279).
53. S. Sparano, R. Gray, M. Oktay, D. Entenberg, T. Rohan, X. Xue, M. Donovan, M. Peterson, A. Shuber, D. Hamilton, T. D'Alfonso, L. Goldstein, F. Gertler, N. Davidson, J. Condeelis, J. Jones, A Novel Metastasis Biomarker (MetaSite Breast™ Score) is Associated with Distant Recurrence in Hormone Receptor-Positive, HER2-Negative Early Stage Breast Cancer. *npj Breast Cancer*, (in press).
54. L. Zhang, S. Riethdorf, G. Wu, T. Wang, K. Yang, G. Peng, J. Liu, K. Pantel, Meta-analysis of the prognostic value of circulating tumor cells in breast cancer. *Clin Cancer Res* 18, 5701-5710 (2012); published online EpubOct 15 (10.1158/1078-0432.CCR-12-1587).
55. J. Y. Pierga, F. C. Bidard, C. Mathiot, E. Brain, S. Delaloge, S. Giachetti, P. de Cremoux, R. Salmon, A. Vincent-Salomon, M. Marty, Circulating tumor cell detection predicts early metastatic relapse after neoadjuvant chemotherapy in large operable and locally advanced breast cancer in a phase II randomized trial. *Clin Cancer Res* 14, 7004-7010 (2008); published online EpubNov 01 (10.1158/1078-0432.CCR-08-0030).

56. W. Onstenk, J. Kraan, B. Mostert, M. M. Timmermans, A. Charehbili, V. T. Smit, J. R. Kroep, J. W. Nortier, S. van de Ven, J. B. Heijns, L. W. Kessels, H. W. van Laarhoven, M. M. Bos, C. J. van de Velde, J. W. Gratama, A. M. Sieuwerts, J. W. Martens, J. A. Foekens, S. Sleijfer, Improved Circulating Tumor Cell Detection by a Combined EpCAM and MCAM CellSearch Enrichment Approach in Patients with Breast Cancer Undergoing Neoadjuvant Chemotherapy. *Mol Cancer Ther* 14, 821-827 (2015); published online EpubMar (10.1158/1535-7163.MCT-14-0653).

57. D. Entenberg, J. Wyckoff, B. Gligorijevic, E. T. Roussos, V. V. Verkhusha, J. W. Pollard, J. Condeelis, Setup and use of a two-laser multiphoton microscope for multichannel intravital fluorescence imaging. *Nat Protoc* 6, 1500-1520 (2011); published online EpubOct (10.1038/nprot.2011.376).

58. D. Entenberg, D. Kedrin, J. Wyckoff, E. Sahai, J. Condeelis, J. E. Segall, Imaging tumor cell movement in vivo. *Current protocols in cell biology editorial board, Juan S. Bonfacino . . . [et al.]* Chapter 19, Unit19 17 (2013); published online EpubMar (10.1002/0471143030.cb1907s58).

59. C. A. Schneider, W. S. Rasband, K. W. Eliceiri, NIH Image to ImageJ: 25 years of image analysis. *Nature methods* 9, 671-675 (2012); published online EpubJul 60. J. B. Wyckoff, J. G. Jones, J. S. Condeelis, J. E. Segall, A critical step in metastasis: in vivo analysis of intravasation at the primary tumor. *Cancer Res* 60, 2504-2511 (2000).

61. C. T. Guy, R. D. Cardiff, W. J. Muller, Induction of mammary tumors by expression of polyomavirus middle T oncogene: a transgenic mouse model for metastatic disease. *Molecular and cellular biology* 12, 954-961 (1992).

62. F. Ahmed, J. Wyckoff, E. Y. Lin, W. Wang, Y. Wang, L. Hennighausen, J. Miyazaki, J. Jones, J. W. Pollard, J. S. Condeelis, J. E. Segall, GFP expression in the mammary gland for imaging of mammary tumor cells in transgenic mice. *Cancer Res* 62, 7166-7169 (2002).

63. P. Thevenaz, U. E. Ruttimann, M. Unser, A pyramid approach to subpixel registration based on intensity. *IEEE transactions on image processing: a publication of the IEEE Signal Processing Society* 7, 27-41 (1998)10.1109/83.650848).

64. P. J. Boimel, T. Smirnova, Z. N. Zhou, J. Wyckoff, H. Park, S. J. Coniglio, B. Z. Qian, E. R. Stanley, D. Cox, J. W. Pollard, W. J. Muller, J. Condeelis, J. E. Segall, Contribution of CXCL12 secretion to invasion of breast cancer cells. *Breast cancer research: BCR* 14, R23 (2012) 10.1186/bcr3108).

65. H. Gil-Henn, A. Patsialou, Y. Wang, M. S. Warren, J. S. Condeelis, A. J. Koleske, Arg/Abl2 promotes invasion and attenuates proliferation of breast cancer in vivo. *Oncogene* 32, 2622-2630 (2013); published online Epub-May 23 (10.1038/onc.2012.284).

66. T. D. Schmittgen, K. J. Livak, Analyzing real-time PCR data by the comparative C(T) method. *Nature protocols* 3, 1101-1108 (2008).

67. Karagiannis G. S., et al., *Neoadjuvant Chemotherapy Induces Breast Cancer Metastasis through a TMEM-Mediated Mechanism*. Sci Trans Med, (Inventors' own manuscript, In Revision, Not Yet Published).

68. Goswami, S., et al., *Breast cancer cells isolated by chemotaxis from primary tumors show increased survival and resistance to chemotherapy*. Cancer Res, 2004. 64(21): p. 7664-7.

69. Wyckoff, J. B., et al., *Direct visualization of macrophage-assisted tumor cell intravasation in mammary tumors*. Cancer Res, 2007. 67(6): p. 2649-56.

70. Hughes, S. K., et al., *PTP1B-dependent regulation of receptor tyrosine kinase signaling by the actin-binding protein Mena*. Mol Biol Cell, 2015. 26(21): p. 3867-78.

71. Leung, E., et al., *Blood vessel endothelium-directed tumor cell streaming in breast tumors requires the HGF C-Met signaling pathway*. Oncogene, 2016.

72. Harney, A. S., et al., *Macrophage tumor cell-dependent motility and vascular permeability are independent processes required for tumor cell intravasation*. 2017.

73. Roussos, E. T., et al., *Mena invasive (MenaINV) promotes multicellular streaming motility and transendothelial migration in a mouse model of breast cancer*. J Cell Sci, 2011. 124(Pt 13): p. 2120-31.

74. Patsialou, A., et al., *Autocrine CSF1R signaling mediates switching between invasion and proliferation downstream of TGFbeta in claudin-low breast tumor cells*. Oncogene, 2014.

75. Patsialou A, B. C. J., Wang Y, Entenberg D, Liu H, Clarke M, Condeelis J S, *Intravital multiphoton imaging reveals multicelluar straming as a crucial component of in vivo cell migration in human breast tumors*. IntraVital, 2013. 2(2): p. e25294-1-14.

76. Harney, A. S., et al., *Real-Time Imaging Reveals Local, Transient Vascular Permeability, and Tumor Cell Intravasation Stimulated by TIE2hi Macrophage-Derived VEGFA*. Cancer Discov, 2015. 5(9): p. 932-43.

77. Gil-Henn, H., et al., *Arg/Abl2 promotes invasion and attenuates proliferation of breast cancer in vivo*. Oncogene, 2013. 32(21): p. 2622-30.

78. Mader, C. C., et al., *An EGFR-Src-Arg-cortactin pathway mediates functional maturation of invadopodia and breast cancer cell invasion*. Cancer Res, 2011. 71(5): p. 1730-41.

79. Harper, K. L., et al., *Mechanism of early dissemination and metastasis in Her2+ mammary cancer*. Nature, 2016 540:589-612. PMID: 27974798.

What is claimed is:

1. A method of reducing chemotherapy-induced metastasis resulting from chemotherapy-induced increased assembly of Tumor MicroEnvironment of Metastasis (TMEM) sites in a subject undergoing chemotherapy treatment of a breast cancer tumor, comprising:
    a) identifying the subject as having an increased risk of metastasis in response to chemotherapy by performing or having performed a quantification of Mena$^{Calc}$, Mena$^{INV}$ or a TMEM score of the tumor, and comparing to a predetermined control level of Mena$^{Calc}$, Mena$^{INV}$ or TMEM score, wherein a subject having a Mena$^{Calc}$, Mena$^{INV}$ or a TMEM score above the respective predetermined control level identifies the subject as having an increased risk of metastasis, and
    b) when a subject is identified in step a) as having an increased risk of metastasis in response to chemotherapy, either (1) ceasing chemotherapy on the subject and administering a targeted therapy, immunotherapy or radiotherapy to treat the cancer, or (2) administering a chemotherapy and an amount of a TMEM inhibitor to the subject effective to treat the tumor.

2. The method of claim 1 further comprising obtaining a predetermined control level for Mena$^{Calc}$, Mena$^{INV}$ or TMEM score for the subject by obtaining a $Mena^{Calc}$, $Mena^{INV}$ or TMEM score from a tumor sample from the subject prior to any chemotherapy being initiated on the subject.

3. The method of claim 1 wherein the TMEM inhibitor comprises a CSF1R inhibitor, a VEGFR inhibitor, or a MENA inhibitor.

4. The method of claim 3 wherein the Mena inhibitor is an interfering-RNA, an interfering-microRNA, a Mena gene edit, or a Mena gene splicing suppressor.

5. The method of claim 3 wherein the Mena inhibitor is a small molecule inhibitor of, or an aptamer which inhibits, Mena's interaction with a target protein.

6. The method of claim 3 wherein the Mena inhibitor is an inhibitor of Mena's interaction with a target protein which is PTP1b, SHIP2, Rac1, or a receptor tyrosine kinase.

7. The method of claim 1 wherein the chemotherapy is a neoadjuvant therapy.

8. The method of claim 1 wherein the chemotherapy is an anti-tubulin chemotherapy.

9. The method of claim 1 wherein the chemotherapy is a taxane.

10. The method of claim 1 wherein the chemotherapy is paclitaxel or eribulin.

11. The method of claim 1 wherein the chemotherapy comprises doxorubicin and cyclophosphamide.

12. The method of claim 1 wherein the breast cancer is an adenocarcinoma.

13. The method of claim 1 wherein the breast cancer is Human Epidermal Growth Factor 2 Negative.

14. The method of claim 1 wherein the breast cancer is a Stage IV breast cancer.

15. The method of claim 1, wherein the metastasis is a lung metastasis, bone metastasis, lymph node metastasis, liver metastasis or brain metastasis.

16. The method of claim 1 wherein the subject is a human subject.

* * * * *